US012788695B2

(12) United States Patent
Akintelure et al.

(10) Patent No.: US 12,788,695 B2
(45) Date of Patent: Nov. 10, 2026

(54) PERSONAL CLEANSING COMPOSITIONS, METHODS AND USES

(71) Applicant: The Procter & Gamble Company, Cincinnati, OH (US)

(72) Inventors: Olubolaji Akintelure, Mason, OH (US); Edward Dewey Smith, III, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 419 days.

(21) Appl. No.: 18/535,131

(22) Filed: Dec. 11, 2023

(65) Prior Publication Data

US 2024/0207154 A1 Jun. 27, 2024

Related U.S. Application Data

(60) Provisional application No. 63/433,074, filed on Dec. 16, 2022.

(51) Int. Cl.

| | |
|---|---|
| ***C11D 1/12*** | (2006.01) |
| ***A61K 8/06*** | (2006.01) |
| ***A61K 8/34*** | (2006.01) |
| ***A61K 8/42*** | (2006.01) |
| ***A61K 8/46*** | (2006.01) |
| ***A61Q 19/10*** | (2006.01) |
| ***C11D 1/14*** | (2006.01) |
| ***C11D 3/50*** | (2006.01) |

(52) U.S. Cl.
CPC .............. *A61K 8/463* (2013.01); *A61K 8/068* (2013.01); *A61K 8/345* (2013.01); *A61K 8/42* (2013.01); *A61Q 19/10* (2013.01)

(58) Field of Classification Search
CPC ........... C11D 1/12; C11D 1/14; C11D 3/2041; C11D 3/2065; C11D 3/50; A61K 8/068; A61K 8/345; A61K 8/463; A61Q 19/10
See application file for complete search history.

(56) References Cited

U.S. PATENT DOCUMENTS

| | | | | |
|---|---|---|---|---|
| 2,438,091 | A | 3/1948 | Lynch | |
| 2,528,378 | A | 10/1950 | Mannheimer | |
| 2,658,072 | A | 11/1953 | Milton | |
| 5,104,646 | A | 4/1992 | Bolich, Jr. | |
| 5,106,609 | A | 4/1992 | Bolich, Jr. | |
| 8,518,991 | B2 | 8/2013 | Gunn | |
| 11,179,301 | B2 | 11/2021 | Smith, III | |
| 2008/0113006 | A1 | 5/2008 | Saito et al. | |
| 2022/0081648 | A1* | 3/2022 | Billiauw | C11D 1/04 |

OTHER PUBLICATIONS

PCT Search Report and Written Opinion for PCT/US2023/083499 dated Apr. 3, 2024, 14 pages.

* cited by examiner

*Primary Examiner* — Brian P Mruk
(74) *Attorney, Agent, or Firm* — Alexandra S. Anoff

(57) ABSTRACT

Described herein, personal cleansing compositions, methods and uses. Personal cleansing compositions can include a surfactant, a perfume, a hydric solvent, and water, wherein the composition is structured.

19 Claims, 6 Drawing Sheets

PERSONAL CLEANSING COMPOSITIONS, METHODS AND USES

This application claims benefit of Provisional Ser. No. 63/433,074, filed on Dec. 16, 2022.

FIELD OF THE INVENTION

The present application generally relates to personal cleansing compositions, its methods and its uses. The personal cleansing composition includes a surfactant comprising a first surfactant and a cosurfactant, a perfume, a hydric solvent and water. The first surfactant includes a specific mixture of C12 and C13 alkyl sulfate anionic surfactants. The composition is structured, and preferably at least a portion of the composition may be in a lamellar phase.

BACKGROUND OF THE INVENTION

Cleansing is an activity that has been done for hundreds of years. Early cleansers were based on either soap chemistry or simple mechanical action in order to remove dirt from the skin, as well as endogenous soils such as sweat, sebum, and body odors. Smelling clean is an important benefit, however, early on, perfume was applied after cleansing as early cleansers were not designed to deposit a consumer preferred amount of perfume on skin. So, the inclusion of large amounts of perfume in a cleansing composition was both wasteful, as it was washed down the drain, and expensive. As skin cleansing compositions have become more complex, providing scent during cleansing and residual scent on the skin after cleansing are expected by users of modern skin cleansers. Personal cleansing compositions comprising sodium trideceth-2 sulfate and a hydric solvent were explored to provide microemulsion phases to deliver fragrance.

Ethoxylated surfactants such as Sodium Laureth Sulfate (SLES or SLE3S) or Sodium Trideceth-n Sulfate (STnS) are used widely across the cosmetic industry in personal cleaning products. These surfactants traditionally have been used to achieve a consumer desirable product profile which includes dispensed viscosity/product texture, lather, cleaning, and deposition of skin actives. Ethoxylation provides enhanced solubility, reduced crystallization in liquids, enhanced polymer interaction for coacervate formation and subsequent benefit delivery to the skin and scalp, increased mildness to the skin, and improved quality of lather.

Alkoxylated fatty alcohols are used are in many industries. For example, they can be used as non-ionic surfactants in detergents and cleansers. They can also be an intermediate in the production of other surfactants through processes like sulfation. Current sulfation processes of alkoxylated fatty alcohols can result in the formation of unwanted impurities such as 1,4-dioxane components as trace residual amounts which can remain as part of the alkoxylated fatty alcohol sulfate as it is sold or used. Such unwanted impurities can be removed by additional treatment processes, e.g. a relatively and costly vacuum stripping process.

Also, 1,4-dioxane is a persistent impurity that forms from ethoxylate surfactants and may result in trace residual amounts being present, particularly during sulfation of ethoxylated fatty alcohols, and in those same ethoxylated surfactants during aging in the supply chain and, more slowly, in finished products that contain them.

As such, there is a desire to make personal cleansing compositions that contain relatively very low amount or no ethoxylated surfactants, to mitigate any undesired impurity profile and any need of any additional treatment processes.

There is a need to develop a formulation approach for personal cleansing compositions that utilize relatively very low or non-ethoxylated surfactants, without having negative consumer noticeable trade-off's.

There is still a need to provide personal cleansing compositions with relatively very low ethoxylated or non-ethoxylated surfactants that can be a rigid and stable gel that can deliver perfume benefits onto the skin.

There is still a need to provide personal cleansing compositions with relatively very low ethoxylated or non-ethoxylated surfactants which can provide similar or improved scent during cleansing and/or residual scent on the skin; and which can retain their effectiveness in cleansing and are easy to dispense and spread on the skin.

SUMMARY OF THE INVENTION

A personal cleansing composition is provided and comprises: i) from about 30% to about 55%, preferably from about 32% to about 52%, more preferably from about 35% to about 50% of a surfactant by weight of the composition, wherein the surfactant comprises a first surfactant and a cosurfactant, wherein the first surfactant comprises a mixture of C12 and C13 alkyl sulfate anionic surfactants, optionally wherein the first surfactant consists essentially of a mixture of C12 and C13 alkyl sulfate anionic surfactants, wherein the mixture of the C12 and C13 alkyl sulfate anionic surfactants comprises a mixture of surfactant isomers of Formula I and surfactant isomers of Formula II:

$$CH_3-(CH_2)_p-CH_2-OSO_3^- X^+ \quad (I)$$

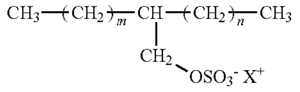

(II)

- wherein $10 \le p \le 11$;
- wherein $8 \le m+n \le 9$ and $0 \le m, n \le 9$;
- wherein X is a counter cation selected from the group consisting of lithium, sodium, potassium and ammonium, preferably sodium;
- wherein the first surfactant comprises: from about 37% to about 50%, preferably from about 38% to about 49%, more preferably from about 40% to about 49% of the C12 alkyl sulfate anionic surfactant by weight of the first surfactant, wherein the C12 alkyl sulfate anionic surfactant comprises a 2-alkyl branched C12 alkyl sulfate; from about 50% to about 63%, preferably from about 51% to about 62%, more preferably from about 51% to about 60% of the C13 alkyl sulfate anionic surfactant by weight of the first surfactant, wherein the C13 alkyl sulfate anionic surfactant comprises a 2-alkyl branched C13 alkyl sulfate; and less or equal than about 5% of other alkyl sulfate anionic surfactants by weight of the first surfactant, preferably less or equal than about 4% of other alkyl sulfate anionic surfactants by weight of the first surfactant, preferably wherein other alkyl sulfate anionic surfactants are not C12 or C13 alkyl sulfate anionic surfactant;

ii) from about 4.5% to about 25%, preferably from about 7% to about 22%, more preferably from about 7.5% to about 19.5% of a perfume by weight of the composition;

iii) from about 6% to about 18.5%, preferably from about 6.5% to about 17%, more preferably from about 7% to about 15% of a hydric solvent by weight of the composition; and iv) water;

wherein the weight ratio of the surfactant to the hydric solvent is greater than or equal to 2.7, preferably greater than or equal to 3.1, more preferably greater than or equal to 3.8, even more preferably from 3.8 to 5.0; wherein the composition is structured, preferably at least a portion of the composition is in a lamellar phase.

A method of providing similar or enhanced in-vitro bloom or fragrance skin deposition of a rinse-off microemulsion cleansing composition, is provided and comprises a combination of a first surfactant and a hydric solvent, including: i) from about 30% to about 55%, preferably from about 32% to about 52%, more preferably from about 35% to about 50% of a surfactant by weight of the composition, wherein the surfactant comprises a first surfactant and a cosurfactant, wherein the first surfactant comprises a mixture of C12 and C13 alkyl sulfate anionic surfactants, optionally wherein the first surfactant consists essentially of a mixture of C12 and C13 alkyl sulfate anionic surfactants, wherein the mixture of the C12 and C13 alkyl sulfate anionic surfactants comprises a mixture of surfactant isomers of Formula I and surfactant isomers of Formula II:

$$CH_3-(CH_2)_p-CH_2-OSO_3^-X^+ \quad (I)$$

(II)

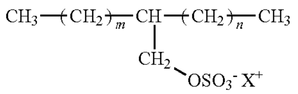

wherein 10≤p≤11;

wherein 8≤m+n≤9 and 0≤m, n≤9;

wherein X is a counter cation selected from the group consisting of lithium, sodium, potassium and ammonium, preferably sodium;

wherein the first surfactant comprises: from about 37% to about 50%, preferably from about 38% to about 49%, more preferably from about 40% to about 49% of the C12 alkyl sulfate anionic surfactant by weight of the first surfactant, wherein the C12 alkyl sulfate anionic surfactant comprises a 2-alkyl branched C12 alkyl sulfate; from about 50% to about 63%, preferably from about 51% to about 62%, more preferably from about 51% to about 60% of the C13 alkyl sulfate anionic surfactant by weight of the first surfactant, wherein the C13 alkyl sulfate anionic surfactant comprises a 2-alkyl branched C13 alkyl sulfate; and less or equal than about 5% of other alkyl sulfate anionic surfactants by weight of the first surfactant, preferably less or equal than about 4% of other alkyl sulfate anionic surfactants by weight of the first surfactant, preferably wherein other alkyl sulfate anionic surfactants are not C12 or C13 alkyl sulfate anionic surfactant;

ii) from about 4.5% to about 25%, preferably from about 7% to about 22%, more preferably from about 7.5% to about 19.5% of a perfume by weight of the composition;

iii) from about 6% to about 18.5%, preferably from about 6.5% to about 17%, more preferably from about 7% to about 15% of a hydric solvent by weight of the composition;

wherein the weight ratio of the surfactant to the hydric solvent is greater than or equal to 2.7, preferably greater than or equal to 3.1, more preferably greater than or equal to 3.8, even more preferably from 3.8 to 5.0; and water to obtain a personal cleansing composition containing a microemulsion phase; then diluting the personal cleansing composition with water at a weight ratio water:composition from about 2:1 to about 10:1, preferably from about 3:1 to about 10:1, more preferably from about 5:1 to about 8:1 to form a rinse-off microemulsion cleansing composition.

Use of a personal cleansing composition as set out herein for providing a stable or improved stable gel.

Use of a first surfactant in a personal cleansing composition, as described hereinbefore for providing a stable or improved stable and rigid gel. The personal cleansing composition has an elastic modulus G' at 1 Hz from about 100 Pa to about 2500 Pa according to the G' and G" Test Method as disclosed herein.

Use of a first surfactant in a personal cleansing composition, as described hereinbefore for providing an improved lather stability.

Use of a first surfactant in a personal cleansing composition, as described hereinbefore for providing a similar or denser lather.

Use of a combination of a first surfactant in a personal cleansing composition, as described hereinbefore and a cosurfactant, wherein the ratio of the weight percent of first surfactant to the weight percent of the cosurfactant is from 4:1 to 20:1, preferably from 5:1 to 9:1, more preferably from 6:1 to 8:1 for providing a similar or denser lather. Preferably, the cosurfactant may comprise a betaine, an alkyl amidopropyl betaine, cocoamidopropyl betaine, and a combination thereof.

Use of a combination between a first surfactant and a hydric solvent in a personal cleansing composition, as described hereinbefore to provide similar or enhance in-vitro bloom of a personal cleansing composition.

Use of a combination of a first surfactant and a hydric solvent in a personal cleansing composition, as described hereinbefore to provide similar or enhance fragrance longevity on skin of a personal cleansing composition.

Use of a combination of a first surfactant and a hydric solvent in a personal cleansing composition, as described hereinbefore to provide similar or enhance fragrance of a personal cleansing composition prior to use.

Use of a combination of a first surfactant and a hydric solvent in a personal cleansing composition, as described hereinbefore to provide similar or enhance fragrance on skin upon initial application of a personal cleansing composition.

BRIEF DESCRIPTION OF THE DRAWINGS

While the specification concludes with claims particularly pointing out and distinctly claiming the present invention, it is believed that the same will be better understood from the following description read in conjunction with the accompanying drawings in which:

DETAILED DESCRIPTION OF THE INVENTION

Definitions of Terms

Figure 1:
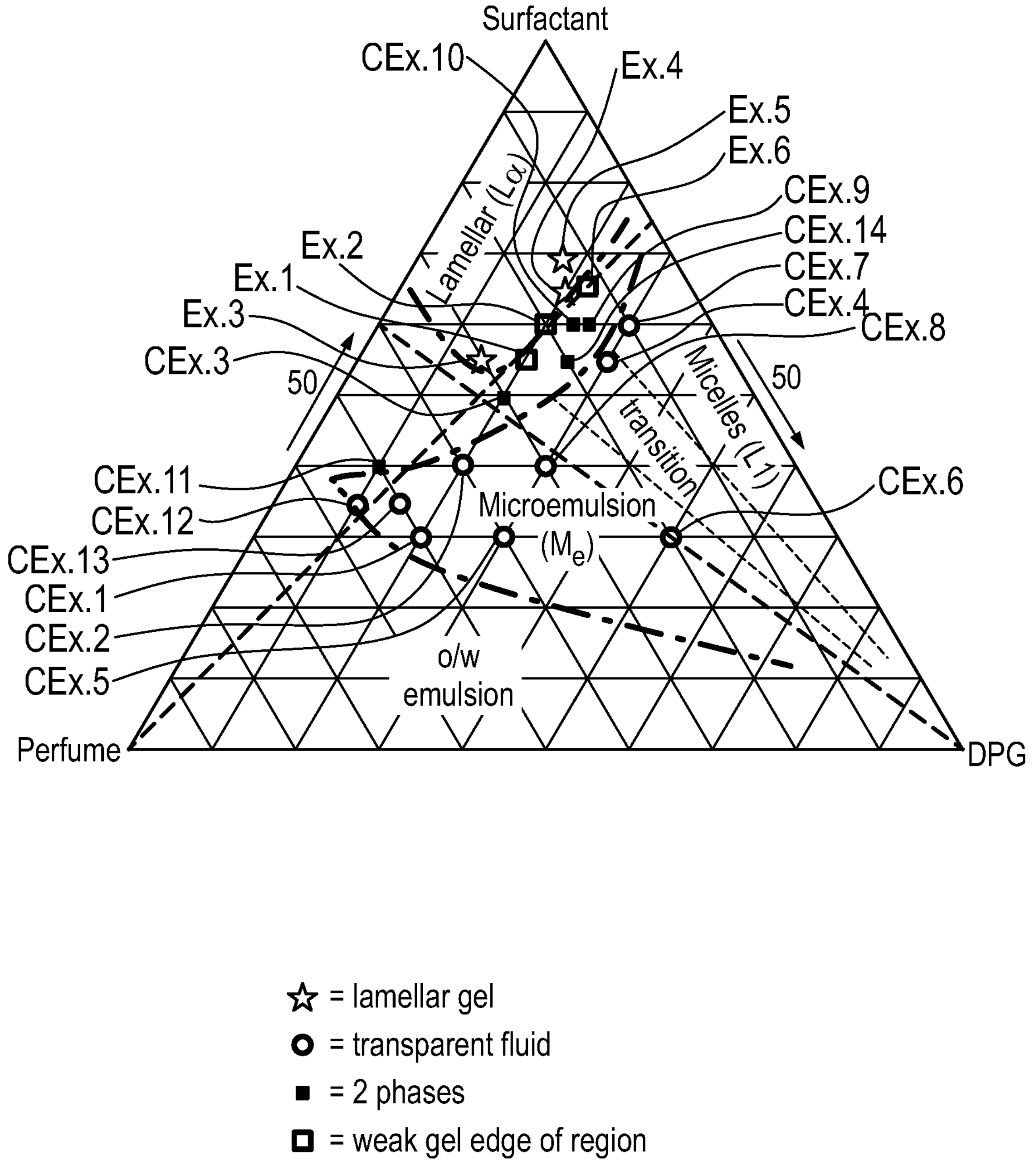
FIG. 1 is a ternary diagram at a constant water percentage of 35% by weight of the composition showing a first surfactant, dipropylene glycol (DPG), and perfume oil.

In this document, including in all embodiments of all aspects of the present invention, the following definitions apply unless specifically stated otherwise.

All percentages are by weight (w/w) of the composition, unless otherwise specified. "% wt." means percentage by weight. References to 'parts' e.g. a mixture of 1 part X and 3 parts Y, is a ratio by weight. All ratios or percentages are weight ratios or weight percentages unless specifically stated otherwise.

An "active composition" is the composition absent water, and an "active ingredient" is the ingredient absent its water.

"QS" or "QSP" means sufficient quantity for 100% or for 100 g.+/− indicates the standard deviation. All ranges are inclusive and combinable. The number of significant digits conveys neither a limitation on the indicated amounts nor on the accuracy of the measurements. All numerical amounts are understood to be modified by the word "about".

All measurements are understood to be made at 25° C. and at ambient conditions, where "ambient conditions" means at 1 atmosphere (atm) of pressure and at 65% relative humidity, unless otherwise stated. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International.

Herein "min" means "minute" or "minutes". Herein "mol" means mole. Herein "g" following a number means "gram" or "grams". "Ex." means "example". All amounts as they pertain to listed ingredients are based on the active level and do not include carriers or by-products that may be included in commercially available materials.

Herein, "comprising" means that other steps and other ingredients can be in addition. "Comprising" encompasses the terms "consisting of" and "consisting essentially of". The compositions, methods, uses, kits, and processes of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated.

As used herein, the articles including "a" and "an" when used in a claim, are understood to mean "one or more" of what is claimed or described.

The terms "include," "includes," and "including," as used herein are meant to be non-limiting.

Where amount ranges are given, these are to be understood as being the total amount of said ingredient in the composition, or where more than one species fall within the scope of the ingredient definition, the total amount of all ingredients fitting that definition, in the composition.

For example, if the composition comprises from 1% to 5% fatty alcohol, then a composition comprising 2% stearyl alcohol and 1% cetyl alcohol and no other fatty alcohol, would fall within this scope.

The amount of each particular ingredient or mixtures thereof described hereinafter can account for up to 100% (or 100%) of the total amount of the ingredient(s) in the composition.

The term "free of" as used herein means that the composition comprises 0% of an ingredient by total weight of the composition, thus no detectable amount of the stated ingredient.

The term "substantially free of" as used herein means less than about 1%, less than about 0.8%, less than about 0.5%, less than about 0.3%, or less than an immaterial amount of by total weight of the composition.

The term "cleansing composition" as used herein refers to compositions intended for topical application to the skin for cleansing.

The term "concentrate/concentrated" as used herein with respect to a cleansing composition refers to a composition where the weight percentage of a surfactant relative to the total composition is greater than about 15%.

The term "C12 alkyl sulfate anionic surfactant" refers to a sulfated anionic surfactant including an alkyl group having a total number of 12 carbon atom numbers.

The term "C13 alkyl sulfate anionic surfactant" refers to a sulfated anionic surfactant including an alkyl group having a total number of 13 carbon atom numbers.

The term "2-branched C12 alkyl sulfate anionic surfactant" as used herein refers to a C12 alkyl sulfate anionic surfactant having an alkyl chain positioned at carbon position 2.

The term "2-branched C13 alkyl sulfate anionic surfactant" as used herein refers to a C13 alkyl sulfate anionic surfactant having an alkyl chain positioned at carbon position 2.

The term "Other branched C12 alkyl sulfate anionic surfactant" as used herein refers to any other branched C12 alkyl sulfate anionic surfactants that are not a 2-branched C12 alkyl sulfate anionic surfactant, like 3-branched or 4-branched or 5-branched, etc., C12 alkyl sulfate anionic surfactant.

The term "Other branched C13 alkyl sulfate anionic surfactant" as used herein refers to any other branched C13 alkyl sulfate anionic surfactants that are not a 2-branched C13 alkyl sulfate anionic surfactant, like 3-branched or 4-branched or 5-branched, etc., C13 alkyl sulfate anionic surfactant.

The term "Other alkyl sulfate anionic surfactant" as used herein refers to any other alkyl sulfate anionic surfactants that are not C12 or C13 alkyl sulfate anionic surfactant, like C11, C14, C15, etc., C16 alkyl sulfate anionic surfactant.

The term "gel" as used herein refers to a material or composition that does not flow under its own weight and has a G' greater than about 25 Pa at 1 Hz in an oscillatory rheology test.

The term "shelf stable gel" as used herein refers to a material or composition that does not flow under its own weight and has a G' from about 25 Pa to less than 90 at 1 Hz in an oscillatory rheology test.

The term "stable gel" as used herein refers to a material or composition that does not separate into more than one phase in a centrifuge test, is able to retain small air bubbles upon standing for 1 day at ambient conditions, and has a G' greater or equal than about 100 Pa at 1 Hz in an oscillatory rheology test.

The term "hydric solvent" as used herein refers to a solvent that is neutral organic species that contains at least 2 hydroxyl groups and is not a hydrotrope.

The term "hydrotrope" as used herein refers to a charged, amphiphilic solubility modifier. Hydrotropes are generally charged olefins especially an olefin sulfonate such as an aromatic sulfonate.

The term "relative bloom" as used herein refers to perfume in the headspace over a composition during use for a perfumed cleansing composition relative to concentration for a conventional, hydric solvent free, control micelle composition having 10 wt. % starting surfactant and 1 wt. % starting perfume when the same perfume is used in the composition and the micelle composition.

The term "in-vitro bloom" as used herein refers to the amount of perfume experienced at a weight ratio at least from 2:1 water to composition dilution versus the amount of perfume in the headspace prior to dilution and can be measured in accordance with Perfumed Headspace Abundance During Dilution Method set out below.

The term "micelle" as used herein refers to a structure comprising individual surfactant molecules aggregated to form a hydrophobic core region with externally facing polar head groups in equilibrium with surfactant monomers in a polar phase, having a characteristic dimension that is about two surfactant lengths, i.e., generally less than about 10 nm in diameter.

The term "microemulsion" as used herein refers to a thermodynamically stable isotropic mixture of oil, surfactant, and water comprising an interior hydrophobic core, having a diameter greater than about twice the extended length of the surfactant molecule, i.e., generally having at least one diameter dimension greater than about 3.5 nm diameter as measured by neutron scattering.

The term "mixtures" as used herein is meant to include a simple combination of materials and any compounds that may result from their combination.

The term "perfume" as used herein refers to a mixture of volatile organic oils having a pleasant aroma wherein the perfume components have individual molecular weights between about 75 and 400 Daltons.

The term "rinse-off" as used herein means the intended product usage includes application to skin followed by rinsing and/or wiping the product from the skin within a few seconds to minutes of the application step. The product is generally applied and rinsed in the same usage event, for example, a shower.

"Room temperature" refers to a temperature of 25° C.

The term "solvent" as used herein refers to species or mixture of species present in a molecular solution in the greatest molar concentration acting in a way to dissolve other species, the latter species generally being larger molecules.

The term "single phase" as used herein when used herein with respect to inventive cleansing compositions refers to homogeneity when measured at the designated temperature in accordance with the Centrifuge Test.

The term "structured" as used herein refers to a personal cleansing composition that may contain more than one phases that do not separate into two or more visible layers or phases in the centrifuge test as disclosed herein; and do not separate upon standing for 24 hr at ambient conditions; and are a gel, preferably a shelf-stable gel, most preferably a stable gel.

The objects of the present invention are to provide personal cleansing products, methods and uses of the products, the structures and the respective compositions as described in the Summary or as described hereinbelow for fulfilling the technical effects or goals as set out herein. These objects and other advantages as may be apparent to those skilled in the art can be achieved through the present invention, which is described in the above Summary of the Invention and Detailed Description of the invention and which is defined in the claims which follow.

Benefits

Chemical impurities are sometimes found in raw materials or products utilizing raw materials. For example, 1,4-dioxane is an undesirable byproduct of detergent making. As an industrial processing solvent or chemical intermediate, 1,4-dioxane has previously been reported to be used in the production of products that may have commercial or consumer applications such as paints, adhesives, detergents, and pesticides. As such 1,4-dioxane may be present as an impurity and may result in trace residual amounts in consumer cosmetics/toiletries, household detergents, pharmaceuticals, foods, agricultural and veterinary products and ethylene glycol-based antifreeze coolants.

Also, 1,4-dioxane is a by-product of the manufacturing process of ethoxylated surfactants produced with ethylene oxide. In other words, 1,4-dioxane is an unwanted chemical formed during the surfactant manufacturing process used to create ingredients such as ethoxylated surfactants and polyethylene glycols.

1,4-dioxane can be formed from an ethoxylated product during an unintended side reaction, known as "intramolecular chain transfer" or "backbiting". Two moles of ethylene oxide are eliminated from the ethoxylated product to form 1,4-dioxane. Backbiting can happen once for every 2 moles of ethylene oxide on the molecule.

Hence, 1,4-dioxane is a persistent impurity that forms from ethoxylate products, particularly during sulfation of ethoxylated fatty alcohols to make ethoxylated surfactants, and in those same ethoxylated surfactants during aging in the supply chain and, more slowly, in finished products that contain them.

The amount of 1,4-dioxane by-product within alkoxylated especially ethoxylated alkyl sulfates can be reduced. Based on recent advances in technology, manufacturers can remove most of the 1,4-dioxane in consumer products through a vacuum stripping process or by improved methods of removing impurities, like 1,4-dioxane from already ethoxylated surfactants.

However, there is a desire to make personal cleansing compositions that contain relatively very low amount or no ethoxylated surfactants, without having negative consumer noticeable trade-off's.

Initially, a comparative non-ethoxylated surfactant, namely non-ethoxylated sodium tridecyl sulfate supplied as tradename Rhodapon® TDS from Solvay or made from sulfation of the corresponding tridecyl alcohol supplied as tradename Exxal® 13 by ExxonMobil has been considered.

However, it was not possible to make a concentrated personal cleansing composition with the requisite level of the comparative surfactant when using the comparative non-ethoxylated surfactant mentioned just above supplied with 35 wt. % water in the composition. Also, the personal cleansing compositions did not have acceptable structured properties.

To provide a rigid and stable gel and high perfume delivery properties, the personal cleansing compositions require a specific first surfactant structure that needs to be found and optimized. Previously, the surfactant structure included the branched alkyl hydrocarbon chains, a hydrophilic ethoxylate spacer, and an anionic sulfate head group in combination with other ingredient components to produce personal cleansing compositions that organize into a structured, lamellar phase that is desirable for dispensing rheology and aesthetics, and which are at the same time capable of diluting into a microemulsion in the presence of water.

The sodium trideceth-n hydrocarbon is a highly branched alkyl sulfate, and able to accomplish all these structure-related needs for high perfume delivery compositions, but in the absence of ethoxylation, inventors have found that it was unable to produce the lamellar phase necessary to deliver desirable use aesthetics. Further, connected to these structural observations, non-ethoxylated sodium tridecyl sulfate that is highly branched was unable to produce a stable lamellar phase, and does not have the resulting elastic modulus, G' for useful product use aesthetics.

Surprisingly, inventors have discovered that when combining selected proportions of a first surfactant comprising a mixture of C12 and C13 alkyl sulfate anionic surfactants, as defined herein with selected proportions and weight ratios of hydric solvent such as dipropylene glycol to surfactant; and perfume, a stable and rigid gel, namely having a lamellar structure could be obtained.

The surfactant comprises a first surfactant and a cosurfactant. The first surfactant comprises a mixture of C12 and C13 alkyl sulfate anionic surfactants. Optionally, the first surfactant may consist essentially of a mixture of C12 and C13 alkyl sulfate anionic surfactants. The mixture of C12 and C13 alkyl sulfate anionic surfactants comprises a mixture of surfactant isomers of Formula I and surfactant isomers of Formula II:

$$CH_3-(CH_2)_p-CH_2-OSO_3^- X^+ \quad (I)$$

(II)

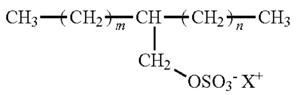

wherein 10≤p≤11;

wherein 8≤m+n≤9 and 0≤m, n≤9;

wherein X is a counter cation selected from the group consisting of lithium, sodium, potassium and ammonium, preferably sodium; wherein the first surfactant comprises: from about 37% to about 50%, preferably from about 38% to about 49%, more preferably from about 40% to about 49% of the C12 alkyl sulfate anionic surfactant by weight of the first surfactant, wherein the C12 alkyl sulfate anionic surfactant comprises a 2-alkyl branched C12 alkyl sulfate; from about 50% to about 63%, preferably from about 51% to about 62%, more preferably from about 51% to about 60% of the C13 alkyl sulfate anionic surfactant by weight of the first surfactant, wherein the C13 alkyl sulfate anionic surfactant comprises a 2-alkyl branched C13 alkyl sulfate; and less or equal than about 5% of other alkyl sulfate anionic surfactants by weight of the first surfactant, preferably less or equal than about 4% of other alkyl sulfate anionic surfactants by weight of the first surfactant, preferably wherein other alkyl sulfate anionic surfactants are not C12 or C13 alkyl sulfate anionic surfactant.

Surprisingly, inventors have found by changing the nature and the distribution of the hydrocarbon branching of a 2-branched alkyl sulfate anionic surfactant, personal cleansing compositions comprising the first surfactant having the mixture of C12 and C13 alkyl sulfate anionic surfactants as described herein are structured and may have especially a structured lamellar phase. Especially, the first surfactant are the sulfated product obtained from commercially available tradenames LIAL®123A alcohol or ISALCHEM®123A alcohol supplied from SASOL.

Personal cleansing compositions comprising the first surfactant having the mixture of C12 and C13 alkyl sulfate anionic surfactants as described herein can lead to a rigid and stable gel that has an elastic modulus G', G" and a tan delta as set out more in details hereinafter. The gel remains stable without any further additions of any ethoxylated anionic surfactants.

Preferably, at least a portion of the composition is in the lamellar phase, or the composition is in the lamellar phase.

The resulting personal cleansing compositions may have a microemulsion phase even at low water content, i.e. without the need of any further dilution.

Also, the personal cleansing compositions may be further diluted into an increased microemulsion phase from a lamellar phase at low water content.

Personal cleansing compositions are easy to dispense and spread on the skin without running off.

To fit with current consumer habits during body cleansing, a personal cleansing composition can be in the form of a stable gel having a structure defined by an elastic modulus, G', a viscous modulus, G", a viscosity, and a shear thinning viscosity ratio as measured by the test methods below. The gel may comprise a lamellar phase, proximal to a micelle composition. In some cases, when the gel has a relatively high perfume concentration in its headspace, it is believed to be in equilibrium with a microemulsion phase, since the gel can evince a characteristic lamellar x-ray diffraction pattern. In other cases, the gel can have a high perfume concentration in the headspace only after dilution water is introduced.

Inventors have found that when G' is below about 25 Pa, the personal cleansing compositions were not fully structured, and not lamellar; and tended to phase separate and become an unstable gel.

As a combination between a surfactant comprising a first surfactant as described herein and a hydric solvent such as dipropylene glycol, inventors have found that the combination of the first surfactant having the mixture of C12 and C13 alkyl sulfate anionic surfactants and hydric solvent is unique in that it has a broad range over which it can help to create the desired structured composition. Also, it may lead to a microemulsion proximal to a lamellar phase in a personal cleansing composition.

Figure 2:
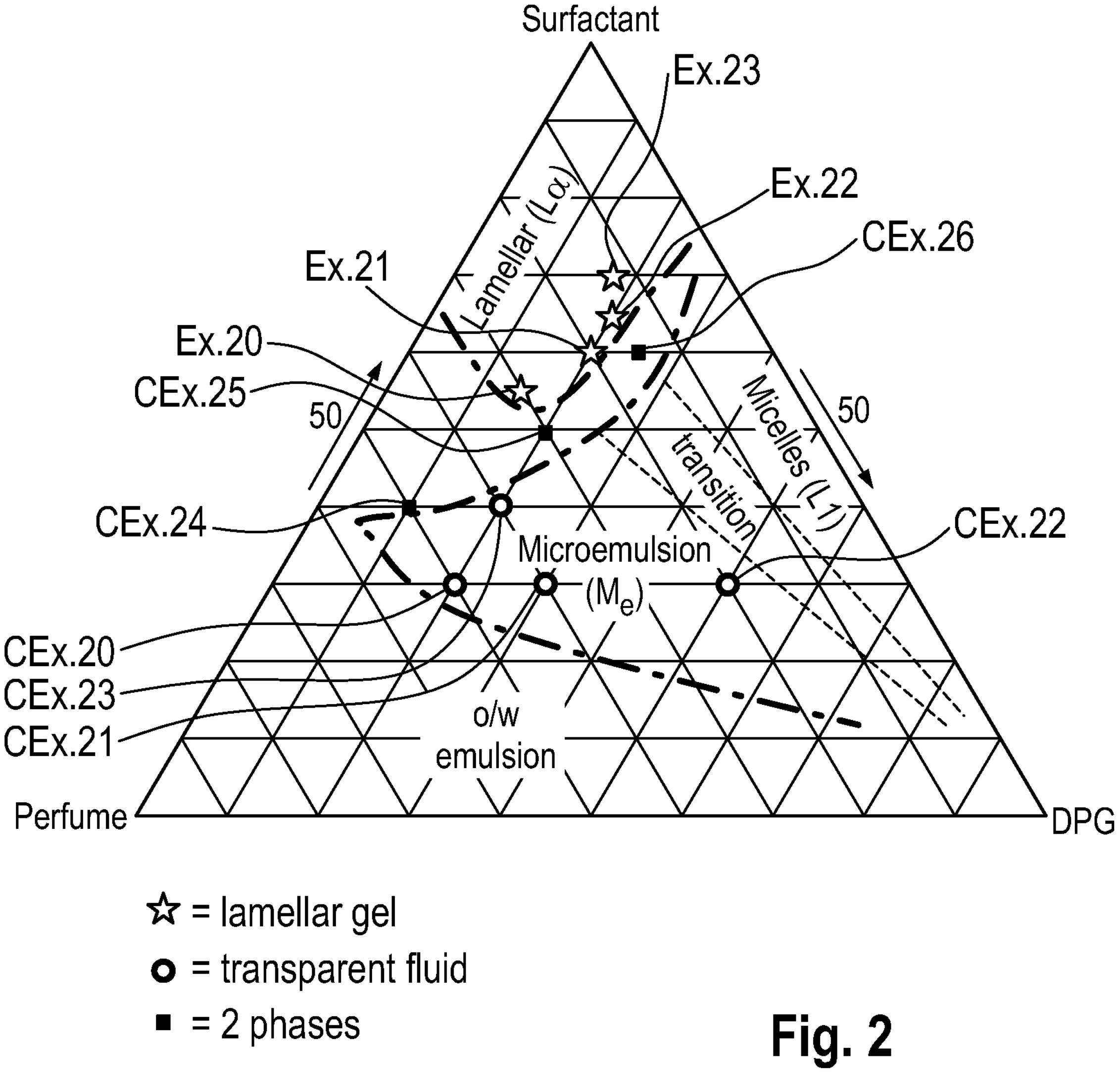
FIG. 2 is a ternary diagram at a constant water percentage of 35% by weight of the composition showing another first surfactant, dipropylene glycol (DPG), and perfume oil.

FIGS. 1 and 2 show the phase diagram for a surfactant comprising two different first surfactants having the mixture of C12 and C13 alkyl sulfate anionic surfactants; and a cosurfactant, preferably when the first surfactant is combined with the cosurfactant from 10:1 to 4:1, such as 6.7:1 weight ratio as an example in FIGS. 1 and 2; combined with a hydric solvent, e.g. dipropylene glycol (DPG) and a representative perfume oil fragrance.

The entirety of the diagram is at 35% water content, the points on the diagram thus constituting the non-water component of the personal cleansing composition. The personal cleansing composition forms a rigid stable gel in the region designated 'Lamellar' above about 50% surfactant, below about 25% DPG and below about 35% fragrance (See FIGS. 1 and 2). When more than about 25% DPG is used, the hydric solvent dissolves the lamellar structure and an additional phase forms, in the two-phase region between lamellar and micelles and between lamellar and microemulsion. A transition region may exist between micelles and microemulsion, which cannot be determined by visual observation or rheology measurements.

When too much fragrance is used, the lamellar phase cannot dissolve all of it, and it becomes a second phase, which is less dense than the lamellar phase so it may be a microemulsion in equilibrium with the lamellar phase.

When too little surfactant is used, especially when too little first surfactant is used while the weight ratio between the first surfactant to cosurfactant remains the same, any structured phase, and lamellar phase do not form, as there is sufficient water and hydric solvent to allow the greater surfactant spacing.

Lather Benefits

Some personal cleansing compositions may form microemulsions but perform poorly for lathering and hence cleaning, which are important features for consumers. Personal cleansing compositions comprising the first surfactant as described herein can also have consumer acceptable lather properties.

Lather can be measured in accordance with the Cylinder Method described below. Compositions may have a lather volume of about 500 mL or more, preferably about 600 mL or more, more preferably from about 630 mL to about 1050 mL. Compositions may have a lather density of about 0.03 g/cc, about 0.04 g/cc, about 0.05 g/cc, 0.055 g/cc, 0.06 g/cc, 0.065 g/cc, or more. Compositions may have a lather mass of about 20 g, about 25 g, about 30 g, about 35 g, about 40 g, about 45 g, or more.

A denser lather can be obtained for personal cleansing compositions comprising the first surfactant as described herein, which is primarily a function of bubble elasticity resulting from improved packing at the interface compared to when the anionic surfactant is sodium trideceth-n sulfate (being either ST2S or ST3S).

Perfume-Related Benefits

Modern consumers of cleansing compositions expect the composition to provide scent both during use and to have residual scent on the skin after use, making perfume an important component of personal cleansing compositions. Perfume is also an important component of many personal cleansing compositions to mask the base odor of cleansing ingredients, which can be unpleasant.

Perfume is composed of mostly hydrophobic oil, whereas personal cleansing compositions generally have an aqueous, continuous phase which provides essentially no ability to carry perfume. It is desirable to provide perfume in a soluble form in a liquid cleansing composition since insoluble phases of any kind can lead to instability problems in the composition. Perfume is therefore generally solubilized within the surfactant component of personal cleansing compositions, such as micelles, lamellar structures, vesicles and the like. Surfactant structures of all kinds contain hydrophobic regions due to the aggregation of surfactant tails, which are able to solubilize significant quantities of perfume oil. Perfume generally exists within the surfactant tails as a molecular solution due to the interaction of the perfume with the surfactant tails, not as a colloidal structure such as an emulsion droplet, which is not thermodynamically stable.

A problem exists in providing perfume scent during use and residual scent to the skin from personal cleansing compositions. Well known physical laws govern the relationship between perfume in the air in equilibrium with perfume solubilized in a micelle or other environment. This relationship is defined by the mole fraction of perfume in the soluble environment, generally the micelle. Micelles are common features of skin cleansers since even non-micellar surfactant compositions generally become micelles during the dilution experienced while cleansing.

Since the perfume concentration in a personal cleansing composition is generally only 25% or less on a molar basis in the surfactant micelle, the vapor pressure of each perfume molecule can be reduced by 75% or even more, due to its solubilization in the micelle. The desire to deliver perfume to the skin suffers from a similar fate during cleansing. Perfume molecules can diffuse, or partition into the skin during cleansing. The driving force to do so is the thermodynamic activity coefficient gradient for the perfume molecules. While a pure perfume applied to the skin, having a high activity coefficient, can partition quickly into skin, perfume located in a surfactant micelle proximal to the skin suffers from an activity coefficient reduction (75% or more) due to micellar solubilization. Therefore most perfume in personal cleansing compositions (about 90%) generally is washed away during rinsing before it can partition into the skin or bloom into the headspace. The result is the skin retains no or very little scent and only for a short duration after a typical cleansing event. Thus, delivery of perfume to the air and to the skin during cleansing is inefficient and therefore expensive.

Overcoming these technical constraints in order to increase perfume delivery to the skin and the bloom of perfume during a cleansing event is not simply a matter of adjusting formula components at increased cost. Natural limits exist related to factors such as solubility. For example, increasing perfume in a personal cleansing composition is not only costly, but is also unfeasible considering the abundance of perfume can become insoluble in the surfactant composition, leading to instability. At some point, the amount of perfume exceeds the capacity of the micelles and the composition becomes unstable and no longer transparent, which is a consumer desirable quality, and the viscosity is reduced. To combat low viscosity and lack of transparency, more surfactant can be added. This approach often results in a composition that is costly to make. In addition, increasing perfume levels in a composition can be harmful to cleaning and stability of the cleansing foam, due to the hydrophobic nature of the perfume oil causing it to behave like a "soil" towards the detergency aspects of the surfactant. Micelle compositions with acceptable viscosity often require as much as 15 wt. % or even 18 wt. % surfactant when 2 wt. % or more perfume is used.

Various means to overcome this problem have been suggested. Perfume microcapsules have been developed to encapsulate perfume and protect it from contact with surfactant. However, only a limited number of perfume molecules are stable in perfume microcapsules; and the perfume microcapsule itself must then be delivered to the skin and, later, mechanically crushed by the consumer in order to release the perfume. Most perfume microcapsules are themselves washed down the drain during cleansing, affording little benefit.

Additionally, personal cleansing compositions have been formulated as micelles. Surfactants have a critical micelle concentration, or CMC, at which they aggregate. Below the CMC surfactant exists as monomers in solution. It has been suggested that dilution to below the CMC can release perfume to increase bloom. The problem with this approach is the CMC is very low, often about 100 ppm for cleansing surfactant mixtures (i.e., 0.01 wt. %, a dilution of more than 500-fold from an original composition). Thus, the CMC occurs at concentrations not relevant to cleansing nor rinsing the body. During rinsing, the CMC is reached only at the very end of cleansing, by which time nearly all the cleansing components have already been washed down the drain in the form of micelles, carrying the perfume with them. Relevant dilutions during cleansing are less than 10-fold, especially less than 5-fold, during which time there is extensive exposure of the wash composition to the body and to the air in the shower, affording both time and opportunity for perfume to bloom and partition to the skin, if it can be removed from the environment of the micelle.

The personal cleansing compositions can also deliver similar or enhanced initial perfume perception, similar or enhanced perfume bloom during cleansing and similar or perfume retention on the skin after cleansing.

Surprisingly, inventors have discovered that the specific first surfactant as described herein together with a hydric solvent at the recited weight ratios between the surfactant and hydric solvent can deliver similar or enhanced initial perfume perception, similar or enhanced perfume bloom during cleansing and similar or enhanced perfume retention on the skin after cleansing.

Without wishing to be limited by theory, the personal cleansing composition comprising the specific first surfactant as described herein can provide the perfume related benefits. Also, the perfume related benefits were believed to result, at least in part, when at least a portion of the perfume in a composition exists in the physical form of a perfume microemulsion within the lamellar phase. This is due to the personal cleansing composition as being structured, and preferably proximal to a microemulsion, that is able to lead to a perfume microemulsion. In the microemulsion form, it is believed most perfume is in a central core region and not close in terms of molecular distance to the surfactant hydrocarbon, therefore it is not in a solvent-solute relationship which can reduce perfume activity coefficient.

The result is bloom and/or relative bloom is similar or significantly enhanced, sometimes doubled or even tripled or more; and scent of perfume over the skin after wash, can be similar or enhanced by a similar magnitude.

The personal cleansing composition may already contain a microemulsion phase. The microemulsion phase may be in equilibrium with the lamellar phase.

Personal cleansing compositions are structured, preferably may be in a lamellar phase and may co-exist with a microemulsion phase or so proximal to a microemulsion phase prior to dilution during use, but can be transformed completely to a perfume microemulsion during use. In fact, there is no need to transform the composition to a perfume microemulsion upon dilution because a microemulsion may already or almost co-exist to provide perfume related benefits.

Optionally, further dilutions of the personal cleansing compositions may lead to an increased microemulsion phase from the lamellar phase.

To make a personal cleansing composition leading to a perfume microemulsion upon dilution, sufficiency of perfume, which is the oil component for making a perfume core; the specific first surfactant as described herein, the right level of the surfactant; and hydric solvents and the weight ratio surfactant to hydric solvent are believed to be the contributing factors. Hydric solvents have multiple effects like, reducing the dielectric of the water phase, acting as a solvent for the surfactant head groups, reducing interfacial tension between the aqueous phase and hydrocarbon, and interacting with the perfume in the core. During use of the personal cleansing composition, as the composition is diluted, hydric solvents are reduced in concentration, the composition begins to transition into a perfume microemulsion because of the abundance of water added during washing and rinsing. This provides a further benefit to increase perfume activity coefficient by increasing perfume molar concentration in the core. Thus, a sufficient amount of hydric solvents in the initial composition will form a microemulsion phase proximal to a lamellar phase, without the need of a further dilution, which can increase perfume activity during use.

Perfume is a benefit agent. Perfume benefits can be realized at different time points for cleansing compositions. Perfume in the package headspace can be important to select a product at the time of purchase. Perfume scent during cleansing, upon introduction of modest amounts of water, such as for example about 3 parts of water per part composition (i.e., a 3:1 dilution ratio), provides a benefit during skin cleansing. During skin cleansing, some perfume can partition into the outer layers of the skin, which can provide a scented skin benefit for a period of time after cleansing, called scent longevity. A governing property for both scent bloom and longevity is the activity coefficient of the perfume molecules, which is a thermodynamic term. Perfume molecules exhibit their maximum vapor pressure only when they are pure. Diluted perfume molecules, whether diluted by surfactant in a micelle, organic solvent, water, etc., exhibit less than their pure vapor pressure. The amount of perfume in a headspace over a composition, diluted composition, or over the skin can be measured analytically, as described in the methods section below. Benefits in initial fragrance intensity, bloom, or longevity can be demonstrated by comparing performance of the compositions before, during, and, or after a skin cleansing event, compared to conventional body wash or shampoo compositions.

Additionally, perfume analysis in the headspace is directly relatable to the perfume solvent environment in a composition or a diluted composition, so that gas chromatography-mass spectrometry (GCMS) headspace measures are an indicator of the perfume environment, i.e., the microemulsion phase and the perfume relationship to solvent molecules therein. Well established physical laws govern the relationship between concentration of molecules in the headspace, and the solvent environment of the molecules in solution, e.g., Raoult's Law. Likewise, headspace measurements over the skin after washing are similarly useful, since perfume partitioning into the skin is enhanced by perfume activity coefficient, as previously discussed.

In addition to being a benefit agent, perfume is an oil and therefore can be a direct contributor to formation of phases responsible for its activity coefficient (as noted above), and therefore to scent bloom and longevity benefits. As discussed above, perfume oil can generally be added into micelle surfactant mixtures only to about 0.25 weight fraction of the surfactant before it phase separates, whereas diluted cleansing compositions described herein can hold at least 0.5 parts perfume:surfactant, or even 0.75 parts perfume:surfactant, or even more, while remaining transparent, including water diluted compositions.

Perfume can be a carrier for non-scented, hydrophobic additives. Additives which are at least 5 wt. %, or at least 10 wt. %, or at least 20 wt. % miscible with perfume may be employed to increase delivery of the additives to the skin.

Any additive which provides a benefit to the skin or the skin environment (e.g., the skin microbiome) may be employed. The additive may provide a direct or indirect benefit, such as antibacterial, antihyperproliferative, anti-inflammatory, chelation, pH regulation, antifungal, antiviral, control of disorders such as acne, atopic dermatitis, eczema, dermatitis, dandruff, antiaging, antiwrinkle, age spot reduction, sunscreen, hydration, moisturization, or any other skin benefit. An advantage of the personal cleansing compositions is enhanced additive delivery to the skin during cleansing. A further benefit is reduction in activity coefficient of the additive by dilution with perfume is transient due to subsequent evaporation of the perfume on the skin, which increases the thermodynamic activity of the additive after its delivery to the skin. Perfume may also provide benefits beyond scent, for example some have antimicrobial activity when delivered to the skin.

Optionally, at least a portion of the personal cleansing composition may be diluted with water at a weight ratio water:composition from about 2:1 to about 10:1, preferably from about 3:1 to about 10:1, more preferably from about 5:1 to about 8:1. The personal cleansing composition may be a rinse-off composition.

Certain microemulsions may be in equilibrium with other phases during dilution of the composition during use. There may be advantages for both the microemulsion and micelle phases to coexist, since micelles may provide superior lather and cleaning properties at the same time the microemulsion may deliver enhanced perfume benefits. Certain analytical measures, such as neutron scattering, dynamic light scattering and optical light transmission, can be used as guides, when evaluating microemulsion phases.

In accordance with the above, a personal cleansing composition comprises a surfactant including a first surfactant and a cosurfactant, a hydric solvent, perfume, and water. Additionally, optional ingredients may also be included as noted herein, for example, preservatives, thickeners, hydrophobic oils, pH modifiers, additives, soap, etc. The personal cleansing composition may not be in the form of a ringing gel. The personal cleansing composition is structured, and may have has at least a portion in a lamellar phase. The personal cleansing composition may be in the form of a microemulsion or may contain a microemulsion phase.

For this, inventors have found that the personal cleansing compositions require a surfactant, a perfume and a hydric solvent in determined proportions to be delivered in a personal cleansing composition that is structured.

Personal Cleansing Compositions

A personal cleansing composition is provided and comprises from about 30% to about 55%, preferably from about 32% to about 52%, more preferably from about 35% to about 50%, most preferably from about 35.5% to about 45.5% of a surfactant by weight of the composition. The surfactant comprises a first surfactant and a cosurfactant. The first surfactant comprises a mixture of C12 and C13 alkyl sulfate anionic surfactants. Optionally, the first surfactant may consist essentially of a mixture of C12 and C13 alkyl sulfate anionic surfactants.

The mixture of the C12 and C13 alkyl sulfate anionic surfactants comprises a mixture of surfactant isomers of Formula I and surfactant isomers of Formula II:

$$CH_3-(CH_2)_p-CH_2-OSO_3^-\ X^+ \qquad (I)$$

-continued (II)

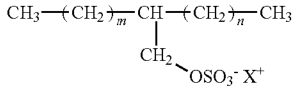

wherein 10≤p≤11;

wherein 8≤m+n≤9 and 0≤m, n≤9;

wherein X is a counter cation selected from the group consisting of lithium, sodium, potassium and ammonium, preferably sodium.

The first surfactant comprises from about 37% to about 50%, preferably from about 38% to about 49%, more preferably from about 40% to about 49% of the C12 alkyl sulfate anionic surfactant by weight of the first surfactant, wherein the C12 alkyl sulfate anionic surfactant comprises a 2-alkyl branched C12 alkyl sulfate.

The first surfactant comprises from about 50% to about 63%, preferably from about 51% to about 62%, more preferably from about 51% to about 60% of the C13 alkyl sulfate anionic surfactant by weight of the first surfactant, wherein the C13 alkyl sulfate anionic surfactant comprises a 2-alkyl branched C13 alkyl sulfate.

The first surfactant also comprises less or equal than about 5% of other alkyl sulfate anionic surfactants by weight of the first surfactant, preferably less or equal than about 4% of other alkyl sulfate anionic surfactants by weight of the first surfactant, preferably wherein other alkyl sulfate anionic surfactants are not C12 or C13 alkyl sulfate anionic surfactant.

The personal cleansing composition also comprises: from about 4.5% to about 25%, preferably from about 7% to about 22%, more preferably from about 7.5% to about 19.5% of a perfume by weight of the composition; from about 6% to about 18.5%, preferably from about 6.5% to about 17%, more preferably from about 7% to about 15% of a hydric solvent by weight of the composition; and water.

The personal cleansing composition also comprises the weight ratio of the surfactant to the hydric solvent is greater than or equal to 2.7, preferably greater than or equal to 3.1, more preferably greater than or equal to 3.8, even more preferably from 3.8 to 5.0.

The personal cleansing composition is structured, preferably at least a portion of the composition is in a lamellar phase.

The lamellar phase of the personal cleansing composition can be characterized by its rheological properties (G', G", tan delta), elasticity, and microscopic birefringence.

The personal cleansing composition may contain a microemulsion phase.

The personal cleansing composition may contain a microemulsion phase, wherein the microemulsion phase is in equilibrium with a lamellar phase.

Alternatively, the personal cleansing composition may further comprise a perfume at a weight ratio perfume: surfactant of at least about 1.5:10, preferably from about 1.5:10 to about 5.5:10, more preferably from about 3:10 to about 5.5:10; and a hydric solvent at a weight ratio hydric solvent:surfactant of at least about 2:10; between about 25% to about 50% water by weight of the composition, wherein the personal cleansing composition has an elastic modulus G' at 1 Hz from about 100 Pa to about 2500 Pa according to the G' and G" Test Method as disclosed herein.

In this alternative, the personal cleansing composition may further comprise a perfume at a ratio of from about 1.5:10 to 5.5:10, preferably from about 2:10 to 5:10, more preferably from about 3:10 to 5:10 to the surfactant, a hydric solvent at a ratio from about 2:10 to 3:9, preferably from about 2:10 to 2.5:8, more preferably from about 2:7 to 2:5 to the surfactant, between about 25% to about 50% water by weight of the composition, wherein the personal cleansing composition has an elastic modulus G' at 1 Hz from about 100 Pa to about 1000 Pa, preferably from about 200 Pa to about 850 Pa, more preferably from about 250 Pa to about 775 Pa according to the Test Method as disclosed herein.

Surfactant

A personal cleansing composition includes a surfactant. Surfactants can help to provide a cleaning benefit, lather properties, and rheology properties to the compositions. The surfactant comprises a first surfactant and a cosurfactant.

The personal cleansing composition comprises from about 30% to about 55%, preferably from about 32% to about 52%, more preferably from about 35% to about 50%, most preferably from about 35% to about 46% of a surfactant by weight of the composition, wherein the surfactant comprises a first surfactant and a cosurfactant.

The total weight percentages of surfactant mentioned previously in the composition include the first surfactant and any cosurfactant.

The personal cleansing composition may include a first surfactant at a level of from about 20% to about 48%, from about 25% to about 45%, or from about 30% to about 40%, or from about 31% to about 40%, or from about 36% to about 40% by weight of the composition.

First Surfactant

The first surfactant as described herein can be used for personal cleansing compositions selected from the group consisting of a personal bar soap, a hand soap, shower gels, a shower or bath cream, a foaming body wash, and mixtures thereof.

The first surfactant comprises a mixture of C12 and C13 alkyl sulfate anionic surfactants. Optionally, the first surfactant may consist essentially of a mixture of C12 and C13 alkyl sulfate anionic surfactants. The mixture of the C12 and C13 alkyl sulfate anionic surfactants comprises a mixture of surfactant isomers of Formula I and surfactant isomers of Formula II:

$$CH_3-(CH_2)_p-CH_2-OSO_3^- X^+ \quad \text{(I)}$$

(II)

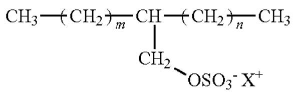

wherein 10≤p≤11;

wherein 8≤m+n≤9 and 0≤m, n 9;

wherein X is a counter cation selected from the group consisting of lithium, sodium, potassium and ammonium, preferably sodium.

The first surfactant comprises from about 37% to about 50% of the C12 alkyl sulfate anionic surfactant by weight of the first surfactant, wherein the C12 alkyl sulfate anionic surfactant comprises a 2-alkyl branched C12 alkyl sulfate. The first surfactant comprises from about 50% to about 63% of the C13 alkyl sulfate anionic surfactant by weight of the first surfactant, wherein the C13 alkyl sulfate anionic surfactant comprises a 2-alkyl branched C13 alkyl sulfate. Also, the first surfactant comprises less or equal than about 5% of other alkyl sulfate anionic surfactants by weight of the first surfactant. Other alkyl sulfate anionic surfactants may be preferably not C12 or C13 alkyl sulfate anionic surfactant.

2-alkyl branched or "beta" branched primary alkyl sulfates are sulfate surfactants that have branching at the C2 position. C1 position is at the carbon atom covalently attached to the sulfate moiety as shown in Formula (II).

Preferably, the first surfactant may comprise from about 38% to about 49% of the C12 alkyl sulfate anionic surfactant by weight of the first surfactant, wherein the C12 alkyl sulfate anionic surfactant comprises a 2-alkyl branched C12 alkyl sulfate. The first surfactant may preferably comprise from about 51% to about 62% of the C13 alkyl sulfate anionic surfactant by weight of the first surfactant, wherein the C13 alkyl sulfate anionic surfactant comprises a 2-alkyl branched C13 alkyl sulfate. The first surfactant may comprise less or equal than about 4% of other alkyl sulfate anionic surfactants by weight of the first surfactant, wherein other alkyl sulfate anionic surfactants are not C12 or C13 alkyl sulfate anionic surfactant.

More preferably, the first surfactant may comprise from about 40% to about 49% of the C12 alkyl sulfate anionic surfactant by weight of the first surfactant, wherein the C12 alkyl sulfate anionic surfactant comprises a 2-alkyl branched C12 alkyl sulfate. The first surfactant may more preferably comprise from about 51% to about 60% of the C13 alkyl sulfate anionic surfactant by weight of the first surfactant, wherein the C13 alkyl sulfate anionic surfactant comprises a 2-alkyl branched C13 alkyl sulfate. The first surfactant may comprise less or equal than about 4% of other alkyl sulfate anionic surfactants by weight of the first surfactant, wherein other alkyl sulfate anionic surfactants are not C12 or C13 alkyl sulfate anionic surfactant.

Most preferably, the first surfactant may comprise from about 43% to about 46% of the C12 alkyl sulfate anionic surfactant by weight of the first surfactant, wherein the C12 alkyl sulfate anionic surfactant comprises a 2-alkyl branched C12 alkyl sulfate. The first surfactant may more preferably comprise from about 51% to about 57% of the C13 alkyl sulfate anionic surfactant by weight of the first surfactant, wherein the C13 alkyl sulfate anionic surfactant comprises a 2-alkyl branched C13 alkyl sulfate. The first surfactant may comprise less or equal than about 3% of other alkyl sulfate anionic surfactants by weight of the first surfactant, wherein other alkyl sulfate anionic surfactants are not C12 or C13 alkyl sulfate anionic surfactant.

As shown in Table 2 more below, an example of a first surfactant is the sulfated product obtained from commercially available tradename LIAL®123A alcohol supplied from SASOL (See also Table 1).

In that example, the first surfactant comprises about 45.2%, or, depending on the commercial batch from the starting alcohol, from about 38% to about 48% of the C12 alkyl sulfate anionic surfactant by weight of the first surfactant, wherein the C12 alkyl sulfate anionic surfactant comprises a 2-alkyl branched C12 alkyl sulfate (at about 23.6% by weight of the first surfactant). The first surfactant comprises from about 51.9%, or, depending on the commercial batch from the starting alcohol, from about 52% to about 62% of the C13 alkyl sulfate anionic surfactant by weight of the first surfactant, wherein the C13 alkyl sulfate anionic surfactant comprises a 2-alkyl branched C13 alkyl sulfate (at about 25.7% by weight of the first surfactant). The first surfactant comprises about 2.9%, or, depending on the commercial batch, from the starting alcohol, less than about 3% of other alkyl sulfate anionic surfactants by weight of the first surfactant, wherein other alkyl sulfate anionic surfactants are not C12 or C13 alkyl sulfate anionic surfactant.

In another example, a first surfactant may be the sulfated product obtained from commercially available tradename ISALCHELM®123A alcohol supplied from SASOL. In that example as shown in Table 3, the first surfactant comprises about 42.8%, or, depending on the commercial batch from the starting alcohol, from about 37% to about 48% of the C12 alkyl sulfate anionic surfactant by weight of the first surfactant, wherein the C12 alkyl sulfate anionic surfactant comprises a 2-alkyl branched C12 alkyl sulfate. The first surfactant comprises from about 55.1%, or, depending on the commercial batch from the starting alcohol, from about 52% to about 63% of the C13 alkyl sulfate anionic surfactant by weight of the first surfactant, wherein the C13 alkyl sulfate anionic surfactant comprises a 2-alkyl branched C13 alkyl sulfate. The first surfactant comprises about 2.1%, or less than about 3% or, depending on the commercial batch from the starting alcohol, of other alkyl sulfate anionic surfactants by weight of the first surfactant, wherein other alkyl sulfate anionic surfactants are not C12 or C13 alkyl sulfate anionic surfactant.

According to the technical data information from the starting alcohol, the first surfactant comprises from about 37% to about 50%, preferably from about 38% to about 49%, more preferably from about 40% to about 49%, most preferably about 43% to about 46% of the C12 alkyl sulfate anionic surfactant by weight of the first surfactant, wherein the C12 alkyl sulfate anionic surfactant comprises a 2-alkyl branched C12 alkyl sulfate. The first surfactant comprises from about 50% to about 63%, preferably from about 51% to about 62%, more preferably from about 51% to about 60%, most preferably from about 51% to about 57% of the C13 alkyl sulfate anionic surfactant by weight of the first surfactant, wherein the C13 alkyl sulfate anionic surfactant comprises a 2-alkyl branched C13 alkyl sulfate. Also, the first surfactant comprises less or equal than about 5%, preferably less or equal than about 4%, more preferably less or equal than about 3% of other alkyl sulfate anionic surfactants by weight of the first surfactant. Other alkyl sulfate anionic surfactants are preferably not C12 or C13 alkyl sulfate anionic surfactant.

The alcohol starting materials can be analyzed by gas chromatography with flame ionization detection (GC/FID).

The samples are typically assessed by diluting the starting Alcohol Example to about 0.1% (v/v) in a volatile alcohol such as methanol or ethanol. The prepared samples were injected (1 μL Injection Volume) into a Splitless Inlet at 280° C. and onto an Agilent DB-1, 30 m×0.250 mm ID, 0.25 μm film thickness capillary GC column. The $H_2$ carrier gas is in constant pressure mode of 0.68 Bar (10.00 psi). The oven temperature program [50° C. (2 min), ramped (10° C./min) to 300° C. (3 min)] has a total run time of 30 minutes. The flame ionization detection (FID) temperature is 320° C. with 30 mL/min $H_2$ flow, 300 mL/min Air flow, and 30 mL/min Makeup ($N_2$) flow.

The sulfation of the alcohol starting materials does not change the alkyl chain distribution in the resulting first surfactant. The first surfactants as sulfates could be separated and analyzed by Ultra High Performance Liquid Chromatography (UHPLC) and detected by both charged aerosol detection (CAD) and high-resolution mass spectrometry (HRMS). However, the results as shown in Table 2 are only indicative since the method is not yet standardized. A plurality of single and pure branched isomers would need to be assessed and quantified by UHPLC-CAD to validate the method.

For Table 2 results, an inverse gradient could be used such that the mobile phase composition at both detectors was constant throughout the separation ensuring that analyte response was not biased differences in organic composition of the mobile phase at the elution time. The CAD response is structure agnostic while electrospray (ESI) MS response may also be influenced by analyte structure. The first surfactants as sulfates possess a hard negative charge that should minimize the variation in ionization efficiency across different branched and chain length species. The ESI MS response is consistent, when the chain length distribution was determined by both UHPLC-CAD and UHPLC-HRMS on First surfactant Example 1. The HRMS provides a molar response, and the CAD provides a mass response. The HRMS data can be converted to mass response for comparison.

The relative chain length distributions for the starting alcohol and the resulted first surfactant comprising a mixture of C12 and C13 alkyl sulfate anionic surfactants are the same with some typical margin errors.

The first surfactant may have an average degree of branching of greater than about 90%, preferably greater than about 92%, more preferably from about 92% to about 100%. Alternatively, the first surfactant may have an average degree of branching from about 40% to about 60% by weight, preferably from about 45% to about 55% by weight, more preferably from about 46% to about 54% by weight, most preferably from about 47% to about 54%.

For instance, the first surfactant may be the sulfated product obtained from commercially available tradename LIAL®123A alcohol supplied from SASOL has an average degree of branching of about 49.4%. Depending on the commercial batch of the starting alcohol, the first surfactant may have an average degree of branching from about 40% to about 60% by weight, preferably from about 45% to about 55% by weight, more preferably from about 46% to about 54% by weight, most preferably from about 47% to about 54%.

As another instance, the first surfactant may be the sulfated product obtained from commercially available tradename ISALCHEM®123A alcohol supplied from SASOL has an average degree of branching of about 92.6%. Depending on the commercial batch of the starting alcohol, the first surfactant may have an average degree of branching of greater than about 90%, preferably of greater than about 92%, more preferably from about 92% to about 100%.

The C12 alkyl sulfate anionic surfactant of the first surfactant may consist of: a) less than about 70% of a linear C12 alkyl sulfate by weight of the C12 alkyl sulfate anionic surfactant; b) more than about 30% of a 2-alkyl branched C12 alkyl sulfate by weight of the C12 alkyl sulfate anionic surfactant, wherein; and c) less than about 10% of other branched C12 alkyl sulfates by weight of the C12 alkyl sulfate anionic surfactant; wherein (a), (b) and (c) add up to about 100% by weight of the C12 alkyl sulfate anionic surfactant.

In that aspect, the 2-alkyl branched C12 alkyl sulfate may comprise more than about 25% of 2-methyl undecyl sulfate by weight the 2-alkyl branched C12 alkyl sulfate; and about 25% or less of 2-ethyl decyl sulfate by weight of the 2-alkyl-branched C12 alkyl sulfate.

Alternatively, the 2-alkyl branched C12 alkyl sulfate may comprise 2-alkyl branched C12 alkyl chains and: more than about 25% of 2-methyl undecyl by weight the 2-alkyl branched C12 alkyl chains; and about 25% or less of 2-ethyl decyl by weight of the 2-alkyl branched C12 alkyl chains.

By C12 alkyl sulfate anionic surfactant, it is meant that the alkyl sulfate anionic surfactant comprises an alkyl chain which consists of 12 carbon atoms. Thus, for blends of alkyl sulfate anionic surfactant having an average chain length of 12 carbon atoms, only those alkyl sulfate anionic surfactants which comprise a C12 alkyl chain fall under the definition of C12 alkyl sulfate anionic surfactant.

For blends of alkyl sulfate anionic surfactant comprising a mixture of different chain lengths including a C12 alkyl subfraction, independent of the average alkyl chain length, solely this C12 alkyl subfraction falls under the definition of C12 alkyl sulfate anionic surfactant.

With regards to the specific degree and type of C2-branching, the C12 alkyl sulfate anionic surfactant may consist of: a) less than or equal to about 60% of the linear C12 alkyl sulfate by weight of the C12 alkyl sulfate anionic surfactant; b) more than or equal to about 40%, of the 2-alkyl branched C12 alkyl sulfate by weight of the C12 alkyl sulfate anionic surfactant; and c) less than about 10% of other branched C12 alkyl sulfates by weight of the C12 alkyl sulfate anionic surfactant; wherein (a), (b) and (c) add up to about 100% by weight of the C12 alkyl sulfate anionic surfactant.

Preferably, the C12 alkyl sulfate anionic surfactant may consist of: a) from about 45% to about 55% of the linear C12 alkyl sulfate by weight of the C12 alkyl sulfate anionic surfactant; b) from about 45% to about 55% of the 2-alkyl branched C12 alkyl sulfate by weight of the C12 alkyl sulfate anionic surfactant; and c) from about 0% to about 5% of other branched C12 alkyl sulfates by weight of the C12 alkyl sulfate anionic surfactant; wherein (a), (b) and (c) add up to about 100% by weight of the C12 alkyl sulfate anionic surfactant.

More preferably, the C12 alkyl sulfate anionic surfactant may consist of: a) from about 45% to 51% of the linear C12 alkyl sulfate by weight of the C12 alkyl sulfate anionic surfactant; b) from about 49% to about 55% of the 2-alkyl branched C12 alkyl sulfate by weight of the C12 alkyl sulfate anionic surfactant; and c) from about 0% to about 5% of other branched C12 alkyl sulfates by weight of the C12 alkyl sulfate anionic surfactant; wherein (a), (b) and (c) add up to about 100% by weight of the C12 alkyl sulfate anionic surfactant.

The above features can be exemplified when the first surfactant is the sulfated product obtained from commercially available tradename LIAL®123A alcohol supplied from SASOL.

Alternatively, for instance when the first surfactant is the sulfated product obtained from commercially available tradename ISALCHEM®123A alcohol supplied from SASOL, the C12 alkyl sulfate anionic surfactant may consist of: a) less than about 10%, preferably less than about 9%, more preferably from about 0% to about 8% of the linear C12 alkyl sulfate by weight of the C12 alkyl sulfate anionic surfactant; b) more than about 90%, preferably more than about 91%, more preferably from about 92% to about 100% of the 2-alkyl branched C12 alkyl sulfate by weight of the C12 alkyl sulfate anionic surfactant; and c) from about 0% to about 5% of other branched C12 alkyl sulfates by weight of the C12 alkyl sulfate anionic surfactant; wherein (a), (b) and (c) add up to about 100% by weight of the C12 alkyl sulfate anionic surfactant.

In that aspect, the 2-alkyl branched C12 alkyl sulfate may comprise more than about 25% of 2-methyl undecyl sulfate by weight the 2-alkyl branched C12 alkyl sulfate; and about 25% or less of 2-ethyl decyl sulfate by weight of the 2-alkyl-branched C12 alkyl sulfate.

In any cases, the 2-alkyl branched C12 alkyl sulfate may comprise: more than about 30% of 2-methyl undecyl sulfate by weight of the 2-alkyl branched C12 alkyl sulfate; less than about 20% of 2-ethyl decyl sulfate by weight of the 2-alkyl branched C12 alkyl sulfate; less than about 20% of 2-propyl nonyl sulfate by weight of the 2-alkyl branched C12 alkyl sulfate; and more than about 25% of 2-butyl octyl sulfate and 2-pentyl heptyl sulfate and other 2-alkyl branched C12 alkyl sulfates by weight of the 2-alkyl branched C12 alkyl sulfate.

Preferably, the 2-alkyl branched C12 alkyl sulfate may comprise: from about 30.5% to about 35% of 2-methyl undecyl sulfate by weight of the 2-alkyl branched C12 alkyl sulfate; from about 15% to about 19.5% of 2-ethyl decyl sulfate by weight of the 2-alkyl branched C12 alkyl sulfate; from about 15% to about 19.5% of 2-propyl nonyl sulfate by weight of the 2-alkyl branched C12 alkyl sulfate; and from about 26% to about 35% of 2-butyl octyl sulfate and 2-pentyl heptyl sulfate and other 2-alkyl branched C12 alkyl sulfates by weight of the 2-alkyl branched C12 alkyl sulfate.

Alternatively, the 2-alkyl branched C12 alkyl sulfate may comprise: more than about 30%, preferably from about 30.5% to about 35% of 2-methyl undecyl by weight of the 2-alkyl branched C12 alkyl chains; less than about 20%, preferably from about 15% to about 19.5% of 2-ethyl decyl by weight of the 2-alkyl branched C12 alkyl chains; less than about 20%, preferably from about 15% to about 19.5% of 2-propyl nonyl by weight of the 2-alkyl branched C12 alkyl chains; and more than about 25%, preferably from about 26% to about 35% of 2-butyl octyl and 2-pentyl heptyl and other 2-alkyl branched C12 alkyl by weight of the 2-alkyl branched C12 alkyl chains.

The distribution of the 2-alkyl branched C12 alkyl sulfate with 2-methyl-1-undecyl sulfate, 2-ethyl-1-decyl sulfate, 2-propyl-1-nonyl sulfate, 2-butyl-1-octyl sulfate, 2-pentyl-1-heptyl sulfate and other 2-alkyl branched C12 alkyl sulfates can be provided either by weight of the 2-alkyl branched C12 alkyl sulfate, or by weight of the C12 alkyl sulfate anionic surfactant, or by weight of the first surfactant.

The C13 alkyl sulfate anionic surfactant of the first surfactant may consist of: d) less than about 60% of a linear C13 alkyl sulfate by weight of the C13 alkyl sulfate anionic surfactant, and e) more than about 40% of a 2-alkyl branched C13 alkyl sulfate by weight of the C13 alkyl sulfate anionic surfactant; and f) less than about 10% of other branched C13 alkyl sulfates by weight of the C13 alkyl sulfate anionic surfactant; wherein (d), (e) and (f) add up to about 100% by weight of the C13 alkyl sulfate anionic surfactant.

In that aspect, the 2-alkyl branched C13 alkyl sulfate may comprise more than about 30% of 2-methyl dodecyl sulfate by weight the 2-alkyl branched C13 alkyl sulfate, and about 25% or less of 2-ethyl undecyl sulfate by weight of the 2-alkyl branched C13 alkyl sulfate.

Alternatively, the 2-alkyl branched C13 alkyl sulfate may comprise 2-alkyl branched C13 alkyl chains, and: more than about 30% of 2-methyl dodecyl by weight the 2-alkyl branched C13 alkyl chains, and about 25% or less of 2-ethyl undecyl by weight of the 2-alkyl branched C13 alkyl chains.

By C13 alkyl sulfate anionic surfactant, it is also meant that the alkyl sulfate anionic surfactant comprises an alkyl chain which consists of 13 carbon atoms. Thus, for blends of alkyl sulfate anionic surfactant having an average chain length of 13 carbon atoms, only those alkyl sulfate anionic surfactants which comprise a C13 alkyl chain fall under the definition of C13 alkyl sulfate anionic surfactant.

For blends of alkyl sulfate anionic surfactant comprising a mixture of different chain lengths including a C13 alkyl subfraction, independent of the average alkyl chain length, solely this C13 alkyl subfraction falls under the definition of C13 alkyl sulfate anionic surfactant.

With regards to the specific degree and type of C2-branching, the C13 alkyl sulfate anionic surfactant may consist of: d) less than about 55% of the linear C13 alkyl sulfate by weight of the C13 alkyl sulfate anionic surfactant; e) more than about 45% of the 2-alkyl branched C13 alkyl sulfate by weight of the C13 alkyl sulfate anionic surfactant; and f) less than about 10% of other branched C13 alkyl sulfates by weight of the C13 alkyl sulfate anionic surfactant; wherein (d), (e) and (f) add up to about 100% by weight of the C13 alkyl sulfate anionic surfactant.

Preferably, the C13 alkyl sulfate anionic surfactant may consist of: d) from about 45% to about 54% of the linear C13 alkyl sulfate by weight of the C13 alkyl sulfate anionic surfactant; e) from about 46% to about 55% of the 2-alkyl branched C13 alkyl sulfate by weight of the C13 alkyl sulfate anionic surfactant; and f) from about 0% to about 5% of other branched C13 alkyl sulfates by weight of the C13 alkyl sulfate anionic surfactant; wherein (d), (e) and (f) add up to about 100% by weight of the C13 alkyl sulfate anionic surfactant.

More preferably, the C13 alkyl sulfate anionic surfactant may consist of: d) from about 48% to about 53% of the linear C13 alkyl sulfate by weight of the C13 alkyl sulfate anionic surfactant; e) from about 47% to about 52% of the 2-alkyl branched C13 alkyl sulfate by weight of the C13 alkyl sulfate anionic surfactant; and f) from about 0% to about 5% of other branched C13 alkyl sulfates by weight of the C13 alkyl sulfate anionic surfactant; wherein (d), (e) and (f) add up to about 100% by weight of the C13 alkyl sulfate anionic surfactant.

The above features can be exemplified when the first surfactant is the sulfated product obtained from commercially available tradename LIAL®123A alcohol supplied from SASOL.

Alternatively, for instance when the first surfactant is the sulfated product obtained from commercially available tradename ISALCHEM®123A alcohol supplied from SASOL, the C13 alkyl sulfate anionic surfactant may consist of: a) less than about 10%, preferably less than about 9%, more preferably from about 0% to about 8% of the linear C13 alkyl sulfate by weight of the C13 alkyl sulfate anionic surfactant; b) more than about 90%, preferably more than about 91%, more preferably from about 92% to about 100% of the 2-alkyl branched C13 alkyl sulfate by weight of the C13 alkyl sulfate anionic surfactant; and c) from about 0% to about 5% of other branched C13 alkyl sulfates by weight of the C13 alkyl sulfate anionic surfactant; wherein (a), (b) and (c) add up to about 100% by weight of the C13 alkyl sulfate anionic surfactant.

In that aspect, the 2-alkyl branched C13 alkyl sulfate may comprise more than about 30% of 2-methyl dodecyl sulfate by weight the 2-alkyl branched C13 alkyl sulfate, and about 25% or less of 2-ethyl undecyl sulfate by weight of the 2-alkyl branched C13 alkyl sulfate.

In any cases, the 2-alkyl branched C13 alkyl sulfate may comprise: more than about 30.5% of 2-methyl dodecyl sulfate by weight of the 2-alkyl branched C13 alkyl sulfate; less than about 20% of 2-ethyl undecyl sulfate by weight of the 2-alkyl branched C13 alkyl sulfate; less than about 20% of 2-propyl decyl sulfate by weight of the 2-alkyl branched C13 alkyl sulfate; and more than about 25% of 2-butyl nonyl sulfate and 2-pentyl octyl sulfate and other 2-alkyl branched C13 alkyl sulfates by weight of the 2-alkyl branched C13 alkyl sulfate.

Preferably, the 2-alkyl branched C13 alkyl sulfate may comprise: from about 31% to about 40% of 2-methyl dodecyl sulfate by weight of the 2-alkyl branched C13 alkyl sulfate; from about 10% to about 18% of 2-ethyl undecyl sulfate by weight of the 2-alkyl branched C13 alkyl sulfate; from about 10% to about 18% of 2-propyl decyl sulfate by weight of the 2-alkyl branched C13 alkyl sulfate; and from about 26% to about 40% of 2-butyl nonyl sulfate and 2-pentyl octyl sulfate and other 2-alkyl branched C13 alkyl sulfates by weight of the 2-alkyl branched C13 alkyl sulfate.

Alternatively, the 2-alkyl branched C13 alkyl sulfate may comprise: more than about 30.5%, preferably from about 31% to about 40% of 2-methyl dodecyl by weight of the 2-alkyl branched C13 alkyl chains; less than about 20%, preferably from about 10% to about 18% of 2-ethyl undecyl by weight of the 2-alkyl branched C13 alkyl chains; less than about 20%, preferably from about 10% to about 18% of 2-propyl decyl by weight of the 2-alkyl branched C13 alkyl chains; and more than about 25%, preferably from about 26% to about 40% of 2-butyl nonyl and 2-pentyl octyl sand other 2-alkyl branched C13 alkyl by weight of the 2-alkyl branched C13 alkyl chains.

Also, the distribution of the 2-alkyl branched C13 alkyl sulfate with 2-methyl-1-dodecyl sulfate, 2-ethyl-1-undecyl sulfate, 2-propyl-1-decyl sulfate, 2-butyl-1-nonyl sulfate, 2-pentyl-1-octyl sulfate and other 2-alkyl branched C13 alkyl sulfates can be provided either by weight of the 2-branched C13 alkyl sulfate anionic surfactant, or by weight of the C13 alkyl sulfate anionic surfactant or by weight of the first surfactant.

As such, the alkyl chains of the C12 and C13 alkyl sulfate anionic surfactants are highly branched, and have a completely different alkyl branching distribution compared to other sulfates derived from complex branched alcohols such as for example the alcohol sold under the Exxal® 13 supplied from ExxonMobil.

The personal cleansing composition may be substantially free, or free of alkoxylated anionic sulfate surfactant. Preferably, the personal cleansing composition may be substantially free, or free of ethoxylated anionic sulfate surfactant.

The first surfactant may be substantially free, or free of alkoxylated anionic sulfate surfactant. In other words, the first surfactant may have an average degree of alkoxylation of less than 0.5, of less than 0.25, preferably less than 0.1, more preferably is free of alkoxylation.

Preferably, the first surfactant may be substantially free, or free of ethoxylated anionic sulfate surfactant. In other words, the first surfactant may have an average degree of ethoxylation of less than 0.5, of less than 0.25, preferably less than 0.1, more preferably is free of ethoxylation.

The C12 alkyl sulfate anionic surfactant may be substantially free, or free of alkoxylated anionic sulfate surfactant. In other words, the C12 alkyl sulfate anionic surfactant may have an average degree of alkoxylation of less than 0.5, of less than 0.25, preferably less than 0.1, more preferably is free of alkoxylation.

Preferably, the C12 alkyl sulfate anionic surfactant may be substantially free, or free of ethoxylated anionic sulfate surfactant. In other words, the C12 alkyl sulfate anionic surfactant may have an average degree of ethoxylation of less than 0.5, of less than 0.25, preferably less than 0.1, more preferably is free of ethoxylation.

The C13 alkyl sulfate anionic surfactant may be substantially free, or free of alkoxylated anionic sulfate surfactant. In other words, the C13 alkyl sulfate anionic surfactant may have an average degree of alkoxylation of less than 0.5, of less than 0.25, preferably less than 0.1, more preferably is free of alkoxylation.

Preferably, the C13 alkyl sulfate anionic surfactant may be substantially free, or free of ethoxylated anionic sulfate surfactant. In other words, the C13 alkyl sulfate anionic surfactant may have an average degree of ethoxylation of less than 0.5, of less than 0.25, preferably less than 0.1, more preferably is free of ethoxylation.

The average degree of alkoxylation is the mol average degree of alkoxylation (i.e., mol average alkoxylation degree) of all the first or C12 or C13 alkyl sulfate anionic surfactant. Hence, when calculating the mol average alkoxylation degree, the moles of first or C12 or C13 non-alkoxylated sulfate anionic surfactant are included:

Mol average alkoxylation degree=($x1$*alkoxylation degree of surfactant 1+$x2$*alkoxylation degree of surfactant 2+ . . . )/($x1$+$x2$+ . . . )

wherein x1, x2, . . . are the number of moles of each alkyl (or alkoxy) sulfate anionic surfactant of the mixture and alkoxylation degree is the number of alkoxy groups in each alkyl sulfate anionic surfactant.

Suitable alkyl sulfate anionic surfactants can be made using the following process.

Alkyl sulfates are typically prepared by the reaction of fatty alcohols with sulfur trioxide ($SO_3$) or its derivatives or by the reaction of unsaturated compounds with sulfuric acid. Processes using sulfur trioxide in particular have gained prominence for fabricating alkyl sulfate anionic surfactants for use in detergent compositions.

Suitable derivatives of sulfur trioxide include sulfur trioxide complexes such as chlorosulfonic acid, sulfuric acid, or sulfamic acid. Sulfur trioxide is preferred since it tends to result in more pure products. The sulfation reaction typically takes place in a continuous process using a cascade, falling film or tube bundle reactor, with the sulfur trioxide being applied in an equimolar or small excess, usually in a temperature range of 20° C. to 60° C., with the reaction temperature being determined at least partially by the solidification point of the fatty alcohol in the reaction. The reaction typically results in the acid form of the resulting alkyl sulfate anionic surfactant, here the first surfactant which is typically neutralized in a subsequent step, using an alkali such as sodium hydroxide, potassium hydroxide, magnesium hydroxide lithium hydroxide, calcium hydroxide, ammonium hydroxide, monoethanolamine, diethanolamine, triethanolamine, monoisopropanolamine, diamines, polyamines, primary amines, secondary amines, tertiary amines, amine containing surfactants, and mixtures thereof.

Also, it is well known that the process of sulfating fatty alcohols to yield alkyl sulfate anionic surfactants also yields various impurities. The exact nature of these impurities depends on the conditions of sulfation and neutralization. Generally, however, the impurities of the sulfation process include one or more inorganic salts, unreacted fatty alcohol, and olefins ("The Effect of Reaction By-Products on the Viscosities of Sodium Lauryl Sulfate Solutions," Journal of the American Oil Chemists' Society, Vol. 55, No. 12, p. 909-913 (1978), C. F. Putnik and S. E. McGuire). The level of non-alkyl sulfate impurities in the alkyl sulfate anionic surfactant of the present invention can be less than about 6% by weight, preferably less than about 4% by weight, and most preferably less than about 2% by weight of the alkyl sulfate anionic surfactant.

Additional Anionic Surfactant

The personal cleansing composition may comprise an additional anionic surfactant. The additional anionic surfactant may be a non-alkoxylated, preferably a non-ethoxylated anionic surfactant. The additional anionic surfactant is different from the first surfactant.

The additional anionic surfactant is different from the first surfactant and may be selected from the group consisting of ammonium lauryl sulfate, ammonium C10-15 alkyl sulfate, ammonium C11-15 alkyl sulfate, ammonium decyl sulfate, ammonium undecyl sulfate, triethylamine lauryl sulfate, triethanolamine lauryl sulfate, monoethanolamine lauryl sulfate, diethanolamine lauryl sulfate, lauric monoglyceride sodium sulfate, sodium lauryl sulfate, sodium C10-15 alkyl sulfate, sodium C11-15 alkyl sulfate, sodium decyl sulfate, sodium undecyl sulfate, potassium lauryl sulfate, potassium C10-15 alkyl sulfate, potassium C11-15 alkyl sulfate, potassium decyl sulfate, potassium undecyl sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, monoethanolamine cocoyl sulfate, sodium tridecyl benzene sulfonate, sodium dodecyl benzene sulfonate, sodium cocoyl isethionate and combinations thereof.

Preferably, the additional anionic surfactant may be selected from the group consisting of ammonium lauryl sulfate, ammonium undecyl sulfate, triethylamine lauryl sulfate, triethanolamine lauryl sulfate, monoethanolamine lauryl sulfate, diethanolamine lauryl sulfate, sodium lauryl sulfate, sodium undecyl sulfate, potassium lauryl sulfate, potassium undecyl sulfate, sodium lauroyl sarcosinate, sodium cocoyl isethionate and combinations thereof.

Most preferred, the additional anionic surfactant may be selected from the group consisting of ammonium lauryl sulfate, triethylamine lauryl sulfate, triethanolamine lauryl sulfate, monoethanolamine lauryl sulfate, diethanolamine lauryl sulfate, sodium lauryl sulfate, potassium lauryl sulfate and combinations thereof, even most preferred sodium lauryl sulfate.

The personal cleansing composition may comprise from about 0.5% to about 10%, preferably from about 1% to about 8%, more preferably from about 2% to about 6%, most preferably from about 2.5% to about 5.5% of an additional anionic surfactant by weight of the composition.

Cosurfactant

The personal cleansing composition may include from about 1.5% to about 10%, preferably from about 3% to about 7.75%, more preferably from about 4.5% to about 6.5% of a cosurfactant by weight of the composition. The cosurfactant may be, for example, a zwitterionic surfactant, an amphoteric surfactant, a nonionic surfactant, or a combination thereof. Suitable amphoteric or zwitterionic surfactants can include those described in U.S. Pat. Nos. 5,104,646 and 5,106,609.

Additional amphoteric detersive surfactants suitable for use in the personal cleansing compositions can include those surfactants broadly described as derivatives of aliphatic secondary and tertiary amines in which an aliphatic radical can be straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378. Other examples of amphoteric surfactants can include sodium lauroamphoacetate, sodium cocoamphoacetate, disodium lauroamphoacetate disodium cocodiamphoacetate, and mixtures thereof. Amphoacetates and diamphoacetates can also be used.

Zwitterionic surfactants suitable for use in the personal cleansing compositions are well known in the art, and include those surfactants broadly described as derivatives of aliphatic quaternary ammonium, phosphonium, and sulfonium compounds, in which aliphatic radicals can be straight or branched chains, and wherein an aliphatic substituent can contain from about 8 to about 18 carbon atoms such that one carbon atom can contain an anionic group, e.g., carboxy, sulfonate, sulfate, phosphate, or phosphonate. Other zwitterionic surfactants can include a betaine, like an alkyl betaine or alkyl amidopropyl betaine, like cocamidopropyl betaine.

Nonionic surfactants suitable for use in the personal cleansing compositions can include those selected from the group consisting of alkyl ethoxylates, alkyl glucosides, polyglucosides (e.g., alkyl polyglucosides, decyl polyglucosides), polyhydroxy fatty acid amides, alkoxylated fatty acid esters, sucrose esters, amine oxides, or mixtures thereof. Some exemplary nonionic surfactants can include cocamide monoethanolamine, decyl glucoside, or a combination thereof.

As noted above, the cosurfactant can include a combination of amphoteric, zwitterionic, and nonionic surfactants. One grouping of exemplary cosurfactants includes sodium lauryl amphoacetate, laurylamidopropyl betaine, cocamidopropyl betaine, lauryl betaine, lauryl amine oxide, or a combination thereof.

Preferably, the cosurfactant may comprise a betaine, an alkyl amidopropyl betaine, cocoamidopropyl betaine, or a combination thereof.

The weight ratio of the first surfactant to the cosurfactant may be from about 4:1 to about 20:1, preferably from about 5:1 to about 9:1, more preferably from about 6:1 to about 8:1, most preferably from about 6.5:1 to about 7:1.

Perfume

A personal cleansing composition includes a perfume. A personal cleansing composition comprises from about 4.5% to about 25%, preferably from about 7% to about 22%, more preferably from about 7.5% to about 19.5%, even more preferably from about 7.5% to about 15% of perfume by weight of the composition.

Perfume may include solvents such as triethyl citrate, isopropyl myristate, dipropylene glycol, or others, to help, for example, with the miscibility of the perfume molecules with each other or to reduce cost. Generally these perfume solvents provide minimal or negligible effects on surfactant compositions as a whole due to the low amount of perfume in the total composition and the amount of solvent in a perfume can be ignored. However, when solvent in the perfume accounts for more than about 5 wt. % of the total hydric solvent in the cleansing composition, it should be accounted for. For example, when a perfume containing 10% hydric solvent is added to a cleansing composition at a level of 10 wt. % and the composition has 10 wt. % of added hydric solvent, the 1 wt. % of hydric solvent from the perfume accounts for a 9% increase in hydric solvent in the cleansing composition (1/11). Since this is more than a 5% change in the hydric solvent in the composition, it can be important. In this case, hydric solvent from the perfume is added (mathematically) to the hydric solvent from other sources added to the composition; and perfume is considered to comprise only the scented molecules and not the solvent, which is subtracted from the wt. % perfume in the composition.

In addition, the weight ratio of perfume to surfactant can impact the ability of the composition to provide an enhanced fragrance benefit. Without being limited by theory, it is believed at least some of the perfume benefits, like bloom and residual scent are derived from an abundance of perfume on the basis of its relation to the surfactant due at least in part to the interaction of the perfume with surfactant as the composition is diluted. Perfume is soluble in surfactant micelles only to about 25% by weight of the surfactant. Above this level, the composition can become unstable unless steps are taken to form a phase to accept the abundance of perfume. However, forming those phases for stability of the perfume circles the composition back to where the perfume is bound within the composition and difficult to release.

As such, a personal cleansing composition may comprise from about 2% to about 90%, preferably from about 4% to about 70%, more preferably from about 5% to about 50%, even more preferably from about 8% to about 60%, even much more preferably from about 10% to about 50%, even much more preferably from about 12% to about 40%, or again even much more from about 15% to about 35%, or most preferably from about 20% to about 30% of perfume by weight of the surfactant.

The perfume may be at a weight ratio perfume:surfactant of less than or equal to about 6:10, preferably from about 1.5:10 to about 5.5:10, more preferably from about 2:10 to about 5:10, even more preferably from about 3:10 to about 5:10.

Perfumes generally contain a broad range of perfume molecules (PRM) having diverse properties. It is an oversimplification to suggest all of the perfume is in a particular location, like in the core of a microemulsion. The real picture is more complex, with perfume molecules in dynamic equilibrium and structures such as micelles and microemulsions can be percolating. Further, some perfume molecules may favor being among surfactant tails or even in the aqueous phase instead of the microemulsion core. In short, all perfume molecules within a perfume mixture do not behave identically. Certain generalizations are useful to explain observed behaviors without inferring that all molecules in a perfume behave identically. For our purposes, a broad array of perfume molecules in a perfume mixture is analyzed by averaging or summing their performance.

Hydric Solvent

A personal cleansing composition includes a hydric solvent. A personal cleansing composition comprises from about 6% to about 18.5%, preferably from about 6.5% to about 17%, more preferably from about 7% to about 15%, most preferably from about 9% to about 13% of the hydric solvent by weight of the composition.

The hydric solvent may be selected form the group consisting of glycerin, dipropylene glycol (a glycol ether), diethylene glycol, dibutylene glycol, hexylene glycol, butylene glycol, pentylene glycol, heptylene glycol, propylene glycol, a polyethylene glycol having a weight average molecular weight below about 500, and a combination thereof. One example of a polyethylene glycol is PEG 300. Isomers are included in the generally descriptive solvents listed, for example, butylene glycol is meant to included 1,2-butanediol and 1,3-butanediol and 1,4-butanediol. When solvents are solid in the pure form (e.g., 1,6-hexanediol), they can be melted during the making process and are effective hydric solvents.

The hydric solvent may be preferably a glycol comprising from 3 to 12 carbon atoms, preferably from 3 to 7 carbon atoms, more preferably from 3 to 4 carbon atoms. The hydric solvent may be preferably a glycol selected from the group consisting of hexylene glycol, butylene glycol, pentylene glycol, heptylene glycol, propylene glycol, and mixtures thereof.

Alternatively, the hydric solvent may be preferably a glycol ether comprising from 4 to 12 carbon atoms. The hydric solvent may be preferably a glycol ether selected from the group consisting of dipropylene glycol, diethylene glycol, dibutylene glycol, and mixtures thereof.

Preferably, the hydric solvent may be selected form the group consisting of dipropylene glycol, diethylene glycol, dibutylene glycol, butylene glycol, pentylene glycol, propylene glycol, and a combination thereof.

More preferably, the hydric solvent may be selected form the group consisting of dipropylene glycol, diethylene glycol, dibutylene glycol, pentylene glycol, propylene glycol, and a combination thereof.

Even more preferably, the hydric solvent may be selected form the group consisting of dipropylene glycol (a glycol ether), pentylene glycol, propylene glycol, and a combination thereof.

Most preferably, the hydric solvent may comprise dipropylene glycol.

The personal cleansing composition may preferably comprise from about 6% to about 18.5%, preferably from about 6.5% to about 17%, more preferably from about 7% to about 15%, most preferably from about 9% to about 13% of dipropylene glycol by weight of the composition.

In addition, a personal cleansing composition may comprise from about 7% to about 60%, or from about 10% to about 55%, or from about 12% to about 50%, or from about 14% to about 48%, or from about 17% to about 45%, or from about 20% to about 42%, or from about 25% to about 40%, or from about 30% to about 35% of hydric solvent by weight of the surfactant. For example, one exemplary cleansing composition will have 11.7% of hydric solvent by weight of the composition, and 45.4% of surfactant by weight of the composition. Hydric solvent levels can be expressed as a percent of the surfactant because the solvent molecules can engage with the surfactant molecules.

An intermediate level of hydric solvent can be used to deliver both a combination of exemplary rheology and perfume delivery properties. Thus, the hydric solvent may be from about 15% to about 40%, preferably from about 17% to about 35%, more preferably from about 20% to about 30%, expressed as a weight percent of the surfactant.

The hydric solvent may be at a weight ratio of the surfactant to the hydric solvent is greater than or equal to about 2.7, or from about 2.7 to about 5.0, or greater than or equal to about 2.8, or greater than or equal to about 2.9, or greater than or equal to about 3.0, or preferably greater than or equal to about 3.1 or from about 3.1 to about 5.0, or greater than or equal to about 3.2 or from about 3.2 to about 5.0, or from about 3.5 to about 5.0, more preferably greater than or equal to about 3.8 or even more preferably from about 3.8 to about 5.0.

The hydric solvent may be at a weight ratio of the surfactant to the hydric solvent is greater than or equal to about 2.7, preferably from about 2.7 to about 5.0, more preferably from about 3.1 to about 5.0, even more preferably from about 3.2 to about 5.0, most preferably from about 3.8 to about 5.0, wherein the hydric solvent may be selected form the group consisting of dipropylene glycol, diethylene glycol, dibutylene glycol, butylene glycol, pentylene glycol, propylene glycol, and a combination thereof, preferably dipropylene glycol.

It has been found that the composition is structured as a rigid gel and can deliver the fragrance onto the skin when the personal cleansing composition comprises the recited level of surfactant, the first surfactant and the specific weight ratio of the surfactant to the hydric solvent as set out before.

Water

A personal cleansing composition includes water. Water may come in with other components or may be added as free water. A personal cleansing composition may comprise from about 1.5% to about 59.5%, or from about 9% to about 54.5%, or from about 15.5% to about 50.5%, or from about 18% to about 50%, or from about 25% to about 45% of water by weight of the composition.

Alternatively, the personal cleansing composition may comprise from about 25% to about 50%, from about 28% to about 45%, from about 30% to about 40% of water by weight of the composition.

Alternatively, the personal cleansing composition may comprise from about 5% to about 50%, preferably from about 12% to about 45%, more preferably from about 20% to about 40% of water by weight of the composition.

In addition, the total weight percent of water and hydric solvent can help to define the amount of solvent phase in which the microemulsion or surfactant structures are distributed. The total amount of solvent phase (approximately, the additive inverse generally of the surfactant level) is a key driver of surfactant phases due to proximity of surfactants. Thus, the composition may comprise from about 5% to about 75%, from about 15% to about 60%, from about 25% to about 55%, from about 30% to about 53% of the combination of water and hydric solvent by weight of the composition.

The pH of the personal cleansing composition may be from about 5 to about 7, preferably from about 5.5 to 6.5.

Rheology—Viscoelasticity and Viscosity

The rheological properties of the personal cleansing compositions can be characterized by viscoelastic parameters and a viscosity. The rheology of a composition can be defined by its G' and G" values, relating to the composition's structure. G' and G" are measured in accordance with the rheological properties, so called G' and G" Test Method discussed herein. G' and G" describe personal cleansing compositions elastic and viscous response to applied stress, characterizing how the material acts when dispensed from a bottle, sitting on the consumers implement or hand, and how a product spreads on application. It also impacts a consumer's perception of the product, for instance products with low G' values flow too readily in use and are associated in consumer perception and can be perceived as dilute. Conversely products with a high G' are associated in consumer perception with concentrated personal cleansing products. At least a portion of the personal cleansing composition is in a lamellar phase.

The personal cleansing composition may be a structured and shelf stable gel and has an elastic modulus G' at 1 Hz from about 30 Pa to about 2500 Pa. Preferably, the personal cleansing composition may be a structured and stable gel and has an elastic modulus G' at 1 Hz from about 100 Pa to about 2000 Pa, more preferably from about 250 Pa to about 1500, even more preferably from about 250 Pa to about 1200 Pa, most preferably from 250 Pa to 775 Pa according to the G' and G" Test Method as disclosed herein.

Most preferred, the personal cleansing composition may be a structured and stable gel and has a tan delta below or equal to about 0.40, or 0.25, or 0.15, or 0.10, preferably a tan delta from about 0.01 to about 0.10, more preferably a tan delta from about 0.03 to about 0.10, even more preferably a tan delta from about 0.05 to about 0.10, most preferably a tan delta from about 0.07 to about 0.10 according to the G' and G" Test Method as disclosed herein.

In addition, the personal cleansing composition should have a viscosity sufficient to allow it to be dispensed from a package onto an implement or directly onto the skin. At least a portion of the personal cleansing composition is in a lamellar phase.

The viscosity of a personal cleansing composition is measured in accordance with the rheological properties, so-called G' and G" Test Method discussed herein. The personal cleansing composition may have a viscosity at about 0.10 l/sec from about 10 Pa·s to about 1200 Pa·s; from about 20 Pa·s to about 1000 Pa·s, from about 30 Pa·s to about 500 Pa·s, or from about 40 Pa·s to about 300 Pa·s.

Alternatively, the personal cleansing composition may have a viscosity at about 10 l/sec of about 1 Pa·s to about 30 Pa·s; from about 1 Pa·s to about 20 Pa·s, from about 1 Pa·s to about 15 Pa·s, or from about 1 Pa·s to about 10 Pa·s.

Compositions can also be highly shear thinning, having a viscosity ratio of less than about 0.20, or 0.10, or even less than 0.05, which is the ratio of the viscosity at 10 l/sec divided by the viscosity at 0.10 l/sec.

Additives

The personal cleansing composition may comprise an additive. Additives are materials that are at least partially soluble in the perfume. It is believed that additives which are at least partially soluble in the perfume will also exhibit a deposition benefit. Additives which are at least about 5 wt. %, or at least about 10 wt. %, or at least about 20 wt. % miscible with perfume may be employed to increase delivery of the additives to the skin. Some examples of classes of material that can be soluble in the perfume are skin actives, vitamins, antibacterials, antifungals, chelants, or combinations thereof.

Examples of skin actives which can be included are sunscreens; anti-acne medicaments; antioxidants; skin soothing agents, skin healing agents; essential oils, skin sensates, anti-wrinkle medicaments, or mixtures thereof. Some examples of skin soothing agents can include, for example, aloe vera, allantoin, bisabolol, dipotassium glycyrrhizinate, or combinations thereof.

Examples of vitamins which can be included are Vitamin A (e.g., beta carotene, retinoic acid, retinol, retinoids, retinyl palmitate, retinyl propionate, etc.), Vitamin B (e.g., niacin, niacinamide, riboflavin, pantothenic acid, etc.), Vitamin C (e.g., ascorbic acid, etc.), Vitamin D (e.g., ergosterol, ergocalciferol, cholecalciferol, etc.), Vitamin E (e.g., tocopherol acetate, tocopherol nicotinate, etc.), Vitamin K (e.g., phytonadione, menadione, phthiocol, etc.), or combinations thereof.

Examples of antibacterials and/or antifungals which can be included are glycolic acid, lactic acid, phytic acid, N-acetyl-L-cysteine, phenoxyethanol, phenoxypropanol, phenoxyisopropanol, zinc pyrithione, octopirox (piroctone olamine), climbazole, ketoconazole, magnalol, hinokitiol, honokitiol, thymol, terpineol, essential oils, or combinations thereof.

Examples of chelants which can be included are 2-aminoethyl phosphoric acid (AEP), N-phosphonomethyl aminodiacetic acid (PMIDA), 1-hydroxyethane-1,1-diphosphonic acid (HEDP), amino tris(methylene phosphonic acid) (ATMP), ethylenediamine tetra(methylene phosphonic acid) (EDTMP), diethylenetriamine penta(methylene phosphonic acid) (DTPMP), phytic acid, nitrilotrimethylene phosphonic acid (NIP), 2-hydroxypyridine oxide (HPNO), or combinations thereof.

The personal cleansing composition may comprise from about 1% to about 20%, from about 2% to about 10%, or from about 3% to about 8% of an additive by weight of the composition.

Hydrophobic Oils

The personal cleansing composition may comprise a hydrophobic oil. Hydrophobic oil can help form a microemulsion phase due to low solubility in the palisade layer of micelles, to further enhance bloom and deposition on skin. The personal cleansing composition may comprise from about 0% to about 25%, from about 2% to about 20%, or from about 3% to about 15% of a hydrophobic oil by weight of the composition. Exemplary hydrophobic oils can include, for example, isopropyl myristate, isostearyl isostearate, behenyl behenate, triglycerides such as soybean oil, hydrocarbon such as mineral oil, or combinations thereof.

Preservatives

Liquid cleansing compositions often have a high water activity (i.e. about 0.95 or more). Water activity describes the availability of water within a composition to support various chemical and biological processes requiring water. Compositions with high water activity can allow growth of microorganisms and therefore generally utilize preservatives. For example, bacteria can grow at a water activity of about 0.90 or above and fungus can grow at a water activity of about 0.70 or above. Below these water activities, microorganisms generally dehydrate and die.

The personal cleansing compositions may have a relatively low water activity, less than about 0.90. The relatively low water activity allows the compositions to naturally resist the growth of microorganisms and thus utilize minimal or even no, preservative. In addition, the use of high levels (5 wt. % or more) of glycols, like dipropylene glycol, can also help to prevent the growth of microorganisms and further support a composition which needs minimal or even no, preservative.

Thickeners

The personal cleansing compositions may comprise from about 0.1% to about 4% of a thickener by weight of the composition. Preferred thickeners are hydrophilic such as cellulose derivatives, hydrophobically modified celluloses, starches and starch derivatives, polyacrylates including hydrophobically modified polyacrylates and polyacrylamides, bacterial polymers such as xanthan gum, tree and plant gums such as guar, insoluble thickeners such as cellulose.

Soap

The personal cleansing compositions as described herein may also comprise a soap.

Packaging

Personal cleansing compositions can be dispensed from a squeezable package with an orifice, such as a conventional body wash or shampoo package. The package can be a compact package, i.e., contain less than about 250 ml, or 200 ml, or 150 ml of volume to signal the contents are concentrated. The shear thinning compositions can be dispensed from a package with a slit valve orifice or other flexible orifice, which is generally cut from a silicone elastomeric material and inserted into an orifice housing.

When the composition has a relatively low viscosity, preferably less than about 0.25 Pa·s, at 10 l/sec, it can be dispensed from a foaming package such as a pump foamer. Compositions can also be dispensed from liquid pump packages.

Methods

In addition to the compositional elements and parameters noted above, it is believed there are also some inventive benefits and/or uses to the compositions which are set out as methods below. For the sake of brevity, all of the compositional elements and parameters noted above are not repeated herein, but can be used within the methods where relevant.

A method for providing a stable or improved stable gel of a personal cleansing composition, comprising, combining i) from about 30% to about 55%, preferably from about 32% to about 52%, more preferably from about 35% to about 50% of a surfactant by weight of the composition, wherein the surfactant comprises a first surfactant and a cosurfactant, wherein the first surfactant comprises a mixture of C12 and C13 alkyl sulfate anionic surfactants, optionally wherein the first surfactant consists essentially of a mixture of C12 and C13 alkyl sulfate anionic surfactants, wherein the mixture of the C12 and C13 alkyl sulfate anionic surfactants comprises a mixture of surfactant isomers of Formula I and surfactant isomers of Formula II:

$$CH_3-(CH_2)_p-CH_2-OSO_3^- X^+ \quad (I)$$

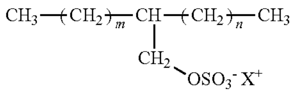

(II)

- wherein 10≤p≤11;
- wherein 8≤m+n≤9 and 0≤m, n≤9;
- wherein X is a counter cation selected from the group consisting of lithium, sodium, potassium and ammonium, preferably sodium;
- wherein the first surfactant comprises: from about 37% to about 50%, preferably from about 38% to about 49%, more preferably from about 40% to about 49% of the C12 alkyl sulfate anionic surfactant by weight of the first surfactant, wherein the C12 alkyl sulfate anionic surfactant comprises a 2-alkyl branched C12 alkyl sulfate; from about 50% to about 63%, preferably from about 51% to about 62%, more preferably from about 51% to about 60% of the C13 alkyl sulfate anionic surfactant by weight of the first surfactant, wherein the C13 alkyl sulfate anionic surfactant comprises a 2-alkyl branched C13 alkyl sulfate; and less or equal than about 5% of other alkyl sulfate anionic surfactants by weight of the first surfactant, preferably less or equal than about 4% of other alkyl sulfate anionic surfactants by weight of the first surfactant, preferably wherein other alkyl sulfate anionic surfactants are not C12 or C13 alkyl sulfate anionic surfactant;
- ii) from about 4.5% to about 25%, preferably from about 7% to about 22%, more preferably from about 7.5% to about 19.5% of a perfume by weight of the composition;
- iii) from about 6% to about 18.5%, preferably from about 6.5% to about 17%, more preferably from about 7% to about 15% of a hydric solvent by weight of the composition; and iv) water;
- wherein the weight ratio of the surfactant to the hydric solvent is greater than or equal to 2.7, preferably greater than or equal to 3.1, more preferably greater than or equal to 3.8, even more preferably from 3.8 to 5.0; wherein the composition is structured, preferably at least a portion of the composition is in a lamellar phase.

A method for providing a similar or denser lather of a personal cleansing composition, comprising, combining; i) from about 30% to about 55%, preferably from about 32% to about 52%, more preferably from about 35% to about 50% of a surfactant by weight of the composition, wherein the surfactant comprises a first surfactant and a cosurfactant, wherein the first surfactant comprises a mixture of C12 and C13 alkyl sulfate anionic surfactants, optionally wherein the first surfactant consists essentially of a mixture of C12 and C13 alkyl sulfate anionic surfactants, wherein the mixture of the C12 and C13 alkyl sulfate anionic surfactants comprises a mixture of surfactant isomers of Formula I and surfactant isomers of Formula II:

$$CH_3-(CH_2)_p-CH_2-OSO_3^- X^+ \quad (I)$$

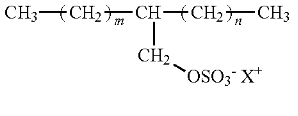

(II)

- wherein 10≤p≤11;
- wherein 8≤m+n≤9 and 0≤m, n 9;
- wherein X is a counter cation selected from the group consisting of lithium, sodium, potassium and ammonium, preferably sodium;
- wherein the first surfactant comprises: from about 37% to about 50%, preferably from about 38% to about 49%, more preferably from about 40% to about 49% of the C12 alkyl sulfate anionic surfactant by weight of the first surfactant, wherein the C12 alkyl sulfate anionic surfactant comprises a 2-alkyl branched C12 alkyl sulfate; from about 50% to about 63%, preferably from about 51% to about 62%, more preferably from about 51% to about 60% of the C13 alkyl sulfate anionic surfactant by weight of the first surfactant, wherein the C13 alkyl sulfate anionic surfactant comprises a 2-alkyl branched C13 alkyl sulfate; and less or equal than about 5% of other alkyl sulfate anionic surfactants by weight of the first surfactant, preferably less or equal than about 4% of other alkyl sulfate anionic surfactants by weight of the first surfactant, preferably wherein other alkyl sulfate anionic surfactants are not C12 or C13 alkyl sulfate anionic surfactant;
- ii) from about 4.5% to about 25%, preferably from about 7% to about 22%, more preferably from about 7.5% to about 19.5% of a perfume by weight of the composition;
- iii) from about 6% to about 18.5%, preferably from about 6.5% to about 17%, more preferably from about 7% to about 15% of a hydric solvent by weight of the composition; and iv) water;
- wherein the weight ratio of the surfactant to the hydric solvent is greater than or equal to 2.7, preferably greater than or equal to 3.1, more preferably greater than or equal to 3.8, even more preferably from 3.8 to 5.0; wherein the composition is structured, preferably at least a portion of the composition is in a lamellar phase.

A method of providing similar or enhanced fragrance or in-vitro bloom or fragrance longevity of a personal cleansing composition, comprising, combining a first surfactant and a hydric solvent, including: i) from about 30% to about 55%, preferably from about 32% to about 52%, more preferably from about 35% to about 50% of a surfactant by weight of the composition, wherein the surfactant comprises a first surfactant and a cosurfactant, wherein the first surfactant comprises a mixture of C12 and C13 alkyl sulfate anionic surfactants, optionally wherein the first surfactant consists essentially of a mixture of C12 and C13 alkyl sulfate anionic surfactants, wherein the mixture of the C12 and C13 alkyl sulfate anionic surfactants comprises a mixture of surfactant isomers of Formula I and surfactant isomers of Formula II:

$$CH_3-(CH_2)_p-CH_2-OSO_3^- X^+ \qquad (I)$$

(II)

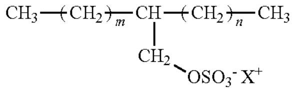

wherein 10≤p≤11;

wherein 8≤m+n≤9 and 0≤m, n≤9;

wherein X is a counter cation selected from the group consisting of lithium, sodium, potassium and ammonium, preferably sodium;

wherein the first surfactant comprises: from about 37% to about 50%, preferably from about 38% to about 49%, more preferably from about 40% to about 49% of the C12 alkyl sulfate anionic surfactant by weight of the first surfactant, wherein the C12 alkyl sulfate anionic surfactant comprises a 2-alkyl branched C12 alkyl sulfate; from about 50% to about 63%, preferably from about 51% to about 62%, more preferably from about 51% to about 60% of the C13 alkyl sulfate anionic surfactant by weight of the first surfactant, wherein the C13 alkyl sulfate anionic surfactant comprises a 2-alkyl branched C13 alkyl sulfate; and less or equal than about 5% of other alkyl sulfate anionic surfactants by weight of the first surfactant, preferably less or equal than about 4% of other alkyl sulfate anionic surfactants by weight of the first surfactant, preferably wherein other alkyl sulfate anionic surfactants are not C12 or C13 alkyl sulfate anionic surfactant;

ii) from about 4.5% to about 25%, preferably from about 7% to about 22%, more preferably from about 7.5% to about 19.5% of a perfume by weight of the composition;

iii) from about 6% to about 18.5%, preferably from about 6.5% to about 17%, more preferably from about 7% to about 15% of a hydric solvent by weight of the composition;

wherein the weight ratio of the surfactant to the hydric solvent is greater than or equal to 2.7, preferably greater than or equal to 3.1, more preferably greater than or equal to 3.8, even more preferably from 3.8 to 5.0; and water to obtain a personal cleansing composition containing a microemulsion phase; then diluting the personal cleansing composition with water at a weight ratio water:composition from about 2:1 to about 10:1, preferably from about 3:1 to about 10:1, more preferably from about 5:1 to about 8:1 to form a rinse-off microemulsion cleansing composition The rinse-off microemulsion cleansing composition may have a G' at 1 Hz of about 100 Pa to about 2500 Pa. The composition may have a total GCMS count higher than that of a control where the hydric solvent is replaced with water, when the total GCMS count is measured in accordance with the PHADD method at zero dilution. The composition may have a GCMS total count of about 10% more than the control, 15%, 20%, 25%, 50%, 75%, 100%, 150%, 200%, 250%, or even 300% more than the control.

Uses

In addition to the compositional elements and parameters noted above, it is believed there are also some inventive benefits and/or uses to the compositions which are set out as uses below. For the sake of brevity, all of the compositional elements and parameters noted above are not repeated herein, but can be used within the uses where relevant.

Use of a personal cleansing composition as set out herein for providing a stable or improved stable and rigid gel.

Use of a first surfactant in a personal cleansing composition, as described hereinbefore for providing a stable or improved stable gel. The personal cleansing composition has an elastic modulus G' at 1 Hz from about 100 Pa to about 2500 Pa according to the G' and G" Test Method as disclosed herein.

Use of a first surfactant in a personal cleansing composition, as described hereinbefore for providing an improved lather stability.

Use of a first surfactant in a personal cleansing composition, as described hereinbefore for providing a similar or denser lather.

Use of a combination of a first surfactant in a personal cleansing composition, as described hereinbefore and a cosurfactant, wherein the ratio of the weight percent of first surfactant to the weight percent of the cosurfactant is from 4:1 to 20:1, preferably from 5:1 to 9:1, more preferably from 6:1 to 8:1 for providing a similar or denser lather. Preferably, the cosurfactant may comprise a betaine, an alkyl amidopropyl betaine, cocoamidopropyl betaine, and a combination thereof.

Use of a combination between a first surfactant and a hydric solvent in a personal cleansing composition, as described hereinbefore to provide similar or enhance in-vitro bloom of a personal cleansing composition.

Use of a combination of a first surfactant and a hydric solvent in a personal cleansing composition, as described hereinbefore to provide similar or enhance fragrance longevity on skin of a personal cleansing composition.

Use of a combination of a first surfactant and a hydric solvent in a personal cleansing composition, as described hereinbefore to provide similar or enhance fragrance of a personal cleansing composition prior to use.

Use of a combination of a first surfactant and a hydric solvent in a personal cleansing composition, as described hereinbefore to provide similar or enhance fragrance on skin upon initial application of a personal cleansing composition.

Test Methods

It is understood that the test methods that are disclosed in the Test Methods Section of the present application should be used to determine the respective values of the parameters of Applicants' invention as such invention is described and claimed herein.

Test Methods a) G' and G" Test Method

To measure the viscoelastic properties of a personal care composition, the viscous (G") and elastic (G') moduli, use a rheometer such as a AR G2 Rheometer (TA Instruments, DE, USA) with serrated flat plate upper geometry with a diameter of 40 mm and serrated flat plate lower geometry with Peltier heating/cooling to control temperature. Place approximately 2 gram of personal care composition onto the lower test geometry and lower the upper geometry to 1050 microns gap, lock the geometry and wipe away excess composition to create an even surface around the edge of the geometry, then continue to the 1 mm measurement gap.

Conduct the oscillatory test over frequency range of 0.1 to 10 Hz, collecting 5 data points per decade, using a constant oscillatory strain of 0.5% and a temperature of 25° C. The tan delta is calculated as the ratio of G"/G'.

Record the G' and G" (Pa) at a frequency of 1 Hz.

b) Centrifuge Test

Compositions are considered to be structured when they do not separate into two or more visible layers or phases when centrifuged for 10 minutes at 3,000 rpm in a standard benchtop swing-rotor at 25° C.

c) Viscosity Method

To measure the viscosity of a personal care composition use a rheometer such as an AR G2 Rheometer (TA Instruments, DE, USA) set up as set out above. Conduct a continuous flow test at 25° C., controlling the shear rate and progressing from a shear rate of 0.01 to 100 l/sec over a time period of 3 minutes, running the test in log mode and collecting 15 points per decade. Record the viscosity (Pa·s) at the shear rates of interest, for the samples herein we have reported the viscosity at a shear rate of about 0.10 l/sec and about 1 l/sec, interpolating as needed to obtain values at shear rates. Fit the data to a Carreau viscosity model and report the zero shear viscosity (Pa·s).

d) Perfume Headspace Abundance During Dilution Method (PHADD)

1) Perfume Headspace Abundance for Neat Products

Unless otherwise indicated, all laboratory instruments are operated according to manufacturer's instructions. The following equipment is used: 20 mL headspace vials from Gerstel (Baltimore, MD); timer; gas chromatograph (GC) Agilent model 6890 and Gerstel MPS-2 auto sampler; GC column J&W DB5-MS, 30 m×0.25 mm ID, 1.0 μm film thickness obtained from Agilent Technologies, Inc., Wilmington, DE, USA; carrier gas of ultra-pure helium, about 1 mL/min. flow rate; solid-phase microextraction injection port liner (0.75 mm ID) from Supelco; and a model 5973 Mass Selective Detector obtained from Agilent Technologies, Inc., Wilmington, DE, USA having a source temperature of about 230° C., and a MS Quad temperature of about 150° C.

1 gram of cleansing composition is placed into a clean 20 mL headspace vial and a stir bar is added to the vial. A polytetrafluroethylene cap is placed on the vial and hand tightened. The sample is allowed to equilibrate to establish equilibrium of the perfume molecules between the composition and the headspace. This generally takes at least 30 minutes at room temperature. The sample is then analyzed using an automated solid phase microextraction-gas chromatograph-mass spectrometer (SPME-GC-MS) analysis system.

Transfer the sample vials to the auto sampler tray to begin analysis. Start the sequence of sample loading and analysis. Each sample vial is taken by the auto sampler to the incubation chamber and held at 30° C. for 1 minute. The SPME fiber assembly is DVB/CAR/PDMS (50/30 um, 24 ga, 1 cm length). Sampling time is 1 minute. The samples are stirred at 500 rpm during SPME sampling. After sampling, the SPME fiber is injected into the GC injector. The injector temperature is about 270° C.

The GC-MS analysis is started. SPME desorption time is about 5 minutes. The following temperature program is used: i) an initial temperature of about 50° C. which is held for 0.5 minutes, and ii) increase the initial temperature at a rate of about 8° C./min until a temperature of about 275° C. is reached, hold at about 275° C. for 2.5 minutes. Perfume compounds are identified using the MS spectral libraries of John Wiley & Sons and the National Institute of Standards and Technology (NIST), purchased and licensed through Agilent. Chromatographic peaks for specific ions are integrated using the MassHunter software obtained from Agilent Technologies, Inc., Wilmington, DE, USA. To calculate the perfume headspace abundance, all of the area counts of the perfume molecules are added together.

2) Perfume Headspace Abundance for Diluted Product

For the perfume headspace abundance for diluted product, use the method above for neat product, except 1.0 g of product is combined with sufficient water to reach the desired level of dilution, usually between (0.5-5 g), a magnetic stir bar is added to each vial, and after the cap is in place, the vials are stirred via the magnetic bar for at least 30 minutes to equilibrate.

e) Perfumed Skin Headspace Abundance Method (PSHAM)

Unless otherwise indicated, all laboratory instruments are operated according to manufacturer's instructions. The following equipment is used: Stir Bar Sorptive Extraction Sampling Devices—Gerstel Twister, 2 cm in length with 1 mm PDMS (polydimethyl silicone) phase thickness; glass sampling cups with magnets to hold Twisters during sampling—about 35 mL in volume; timer; gas chromatograph (GC) Agilent model 7890 and Gerstel MPS-2 autosampler with thermal desorption unit (TDU) and cooled-on-column (CIS-4) temperature programmable inlet; GC column J&W DB5-MS, 30 m×0.25 mm ID, 1.00 μm film thickness obtained from Agilent Technologies, Inc., Wilmington, DE, USA; carrier gas of ultra-pure helium, about 1 mL/min. flow rate; liquid nitrogen for injection port cryogenic cooling; Gerstel TDU injection port liners with glass wool; and a detector model 5975 Mass Selective Detector obtained from Agilent Technologies, Inc., Wilmington, DE, USA having a source temperature of about 230° C., and a MS Quad temperature of about 150° C.

Headspace samples are collected from panelists' arms that have been washed with test products and/or controls. The wash protocol includes: 1) adjusting water temperature to about 37.8° C. (100° F.) and water flow to about 1 gallon/min; 2) rinsing the arm under the water stream for about 5 seconds; 3) apply product of known weight on a puff which has been prewetted for 5 seconds with water; 4) lather product in the puff by hands for 10 seconds; 5) wash the entire forearm for 15 seconds using back and forth motion, then wait for about 15 seconds; 6) rinse the arm under the water stream for about 15 seconds; 7) pat dry the forearm using a paper towel; and then 8) proceed to sensory evaluation or analytical sampling. The Twister device is held inside of the sampling cup with magnetic force while the cup is placed against panelists' arms for a period of 3 minutes. The Twister is then transferred to the thermal desorption tube and capped with a transport adapter.

To begin the analysis, transfer the Twister transport tubes to the autosampler tray and proceed with TDU-GC-MS analysis. Set-up the sequence of samples needing to be analyzed and start the sequence of sample loading and analysis. In this step, the Twister transport tube is taken by the autosampler to the thermal desorption unit where it is heated to about 250° C. and held at that temperature for about 5 minutes. Perfume materials that are thermally desorbed from the Twister are trapped by the liquid nitrogen cooled inlet, which is held at about −120° C. during desorption. The programmable temperature inlet is then heated 275° C. and held at that temperature for 3 minutes.

The GC-MS analysis run is started and the GC temperature program is initiated with mass spectrometer detection. The following temperature program is used: i) an initial temperature of about 50° C. which is held for 0.5 minutes, and ii) increase the initial temperature at a rate of about 8° C./min until a temperature of about 275° C. is reached, hold at about 275° C. for 5 minutes. Perfume compounds are identified using the MS spectral libraries of John Wiley & Sons and the National Institute of Standards and Technology (NIST), purchased and licensed through Agilent. Chromatographic peaks for specific ions are integrated using the MassHunter software obtained from Agilent Technologies, Inc., Wilmington, DE, USA. Abundance of perfume in the headspace over the skin is calculated by adding the area counts of all the perfume molecules. The relative enhancement of abundance of perfume in the headspace using test products over control products is obtained by the ratio of the total peak area counts. The PSHAM measurement may be repeated on the target surface at later time intervals to test for longevity of fragrance on the skin. These time intervals could be any desired, for example, 1 hour, 2 hours, 3 hours, 3.5 hours, 4 hours, etc. after the initial application.

f) Cylinder Method

Lather can be measured in accordance with the Cylinder Method. Lather volume is measured using a graduated cylinder and a rotating mechanical apparatus. A 1,000 ml graduated cylinder is used which is marked in 10 ml increments, has a height of 14.5 inches at the 1,000 ml mark from the inside of its base, and has a neck at its top fitted for a plastic insert cap (for example, Pyrex No. 2982). Moderately hard water (about 7 gpg or about 120 ppm) is prepared by dissolving 1.14 grams calcium chloride dihydrate and 1.73 grams magnesium chloride hexahydrate into one U.S. gallon distilled water. The water is maintained at between 40.5-43.3° C. (105-110° F.). The graduated cylinder is heated to about the same temperature by flushing with excess tap water at the same temperature for about 15 seconds, then drying its exterior and shaking briefly upside down to dry the interior. 100.0 grams of the moderately hard water at the indicated temperature is weighed directly into the graduated cylinder. The cylinder is clamped in a mechanical rotating device, which clamps the cylinder vertically with an axis of rotation that transects the center of the graduated cylinder. Using a 3- or 4-place metric balance, invert the plastic cap for the graduated cylinder onto the balance pan and weigh 0.500 grams of composition for compositions less than 19% surfactant (weigh 0.250 grams of composition for compositions greater or equal than 19% surfactant) to within 4 milligrams accuracy, using a holder to keep the cap level. Insert the cap into the graduated cylinder neck while being careful that all composition is now in the space in the cylinder interior. For compositions with very low viscosity which will not remain on the cap surface, 500 mg composition can be added directly to the graduated cylinder. Rotate the cylinder for 25 complete revolutions at a rate of about 10 revolutions per 18 seconds to create a lather and stop in a level, vertical position. When the cylinder stops in a vertical position, start a digital stopwatch. Observing the water draining at the bottom, record the time to the nearest second when the water height measures 50 cc, then 60 cc, then 70 cc and so on until at least 90 cc has drained. Measure and record the total height of the foam in the column interior, which is the lather volume. If the top surface of the lather is uneven, the lowest height at which it is possible to see halfway across the graduated cylinder is the lather volume (ml). If the lather is coarse such that a single or only a few foam cells ("bubbles") reach across the entire cylinder, the height at which at least about 10 foam cells are required to fill the space is the lather volume, also in ml up from the base. When measuring the lather height, bubbles that are larger than about 25.4 mm (1 inch) across at the top surface are considered free air and not lather. The measurement is repeated and at least three results averaged to obtain the lather volume. In a spreadsheet, calculate the lather density at each observed time point as the volume of foam (total height minus water height) divided by the weight of the foam (100.5 grams minus the weight of water observed, using a density of 1.00 g/cc for water). Fit the 3 time points closest to (ideally, also bracketing) 20 seconds to a $2^{nd}$ order polynomial equation. Solve the equation for the lather density at 20 seconds, which is the lather density of the composition. Multiply the lather volume by the lather density to obtain the lather mass, in grams.

The entire measurement process should take less than about 3 minutes in order to maintain desired temperature.

g) Aging Stability Test

A composition is filled into a 118.3 mL (4 fl. oz.) glass jar with minimal headspace and capped, placed in a dark room maintained at 40° C. for 3 months. A composition is stable if there is minimal visual sign of phase separation and the viscosity changes by less than about 90% from the original viscosity.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

Examples of Suitable Alkyl Sulfate Anionic Surfactants and their Synthesis

The following are representative and non-limiting examples of suitable first surfactant comprising a mixture of C12 and C13 alkyl sulfate anionic surfactants, including a non-limiting method of synthesis from a corresponding starting alcohol. The corresponding starting alcohol comprises the corresponding mixture of C12 and C13 alcohols.

Using the above-described process using sulfur trioxide, the starting alcohols described below as Alcohol Examples 1 and 2 are commercially available and analyzed by gas chromatography with flame ionization detection (GC/FID) as indicated below:

The samples are typically assessed by diluting the starting Alcohol Example to about 0.1% (v/v) in a volatile alcohol such as methanol or ethanol. The prepared samples were injected (1 μL Injection Volume) into a Splitless Inlet at 280° C. and onto an Agilent DB-1, 30 m×0.250 mm ID, 0.25 μm film thickness capillary GC column. The $H_2$ carrier gas is in constant pressure mode of 0.68 Bar (10.00 psi). The oven temperature program [50° C. (2 min), ramped (10° C./min) to 300° C. (3 min)] has a total run time of 30 minutes. The flame ionization detection (FID) temperature is 320° C. with 30 mL/min $H_2$ flow, 300 mL/min Air flow, and 30 mL/min Makeup ($N_2$) flow.

The non-limiting starting alcohols were:

Alcohol Example 1. Tradename LIAL®123A alcohol commercially available from SASOL.

Alcohol Example 2. Tradename ISALCHEM®123A alcohol commercially available from SASOL.

First Surfactant Example 1. Synthesis of First Surfactant Alkyl Sulfate Using a Falling Film Sulfation Reactor The alcohol from Alcohol Example 1 was sulfated in a falling film using a Chemithon single 15 mm×2 m tube reactor using $SO_3$ generated from a sulfur burning gas plant operating at 2.4 kg/h (5.3 lb/hr) sulfur to produce 3.56% $SO_3$ on a volume basis. Alcohol feed rate was 14.2 kg/hour (31.33 lb/hr) and feed temperature was 37.8° C. (100° F.). Conversion of the alcohol to alcohol sulfate acid mix was achieved with 97.75% completeness. Neutralization with 50% sodium hydroxide was completed at ambient process temperature to 0.55% excess sodium hydroxide. 124.9 L (33 gallons) of the sodium neutralized first surfactant sulfate paste. Analyses by standard Cationic $SO_3$ titration method determined final average product activity to be 69.8%.

First Surfactant Example 2. Synthesis of Another First Surfactant Alkyl Sulfate Using a Falling Film Sulfation Reactor The same protocol as for First Surfactant Example 1 was used to prepare First Surfactant Example 2 from the alcohol from Alcohol Example 2. Analyses by standard Cationic $SO_3$ titration method determined final average product activity to be 28.3%.

The effect of type of branching within the alkyl chain of the first surfactant comprising a mixture of C12 and C13 alkyl sulfate anionic surfactants was evaluated for performance within personal cleansing formulations in terms of gel stability, structured features, lather stability, miscibility and perfume benefits, following the test methods described hereinabove.

Test Materials:

The relative performance was determined for the first surfactant comprising a mixture of C12 and C13 alkyl sulfate anionic surfactants based on the starting alcohol summarized in Table 1. The starting Alcohol Example 1 in Table 1 comprised, or consisted essentially of C12 and C13 alkyl chains. Alcohol Example 1 used to make the first surfactant in the inventive composition has a type of branching as described in the claims and were produced following the making process described herein.

The Alcohol Example 1 was commercially available as tradename LIAL®123A alcohol supplied from SASOL and was analyzed by gas chromatography with flame ionization detection (GC/FID) as set out above. The alkyl chain distribution is provided in Table 1.

TABLE 1

Alkyl chain distribution of starting Alcohol Example 1. LIAL ®123A alcohol commercially available from SASOL

| | Alcohol Example 1 |
|---|---|
| Alkyl chain length | C12 |
| Total C12 Alcohol[1] | 45.6% |
| Linear content C12 Alcohol[1] | 21.9% |
| 2-Alkyl Branched C12 Alcohol[1] | 23.7% |
| 2-Alkyl Branch C12 distribution: | |
| 2-methyl-1-undecanol[1] | 7.7% |
| 2-ethyl-1-decanol[1] | 4.1% |
| 2-propyl-1-nonanol[1] | 4.3% |
| 2-butyl-1-octanol, 2-pentyl-1-heptanol, other 2-Alkyl Branched C12 Alcohol[1] | 7.6% |

TABLE 1-continued

Alkyl chain distribution of starting Alcohol Example 1. LIAL ®123A alcohol commercially available from SASOL

| | Alcohol Example 1 |
|---|---|
| Alkyl chain length | C13 |
| Total C13 Alcohol[1] | 53.9% |
| Linear content[1] | 27.9% |
| 2-Alkyl Branched C13 Alcohol[1] | 26.0% |
| 2-Alkyl Branch C13 distribution: | |
| 2-methyl-1-dodecanol[1] | 9.2 |
| 2-ethyl-1-undecanol[1] | 3.9 |
| 2-propyl-1-decanol[1] | 3.8 |
| 2-butyl-1-nonanol, 2-penty1-1-octanol, other 2-Alkyl Branched C13 Alcohol[1] | 9.1 |
| Other[1, 6] | 0.5% |
| TOTAL[1] | 100% |
| Degree of branching | 49.7% |
| Alkyl chain length | C12 |
| Linear content C12 alcohol[2] | 48.0% |
| 2-Alkyl Branched C12 alcohol[2] | 52.0% |
| Total C12 alcohol[2] | 100% |
| 2-Alkyl Branch C12 distribution: | |
| 2-methyl-1-undecanol[3] | 32.5% |
| 2-ethyl-1-decanol[3] | 17.3% |
| 2-propyl-1-nonanol[3] | 18.2% |
| 2-butyl-1-octanol, 2-pentyl-1-heptanol, other 2-Alkyl Branched C12 alcohol[3] | 32.0% |
| Alkyl chain length | C13 |
| Linear content C13 alcohol[4] | 51.8% |
| 2-Alkyl Branched C13 alcohol[4] | 48.2% |
| Total C13 alcohol[4] | 100% |
| 2-Alkyl Branched C13 distribution: | |
| 2-methyl-1-dodecanol[5] | 35.4% |
| 2-ethyl-1-undecanol[5] | 15.0% |
| 2-propyl-1-decanol[5] | 14.6% |
| 2-butyl-1-nonanol, 2-pentyl-1-octanol, other 2-Alkyl Branched C13 alcohol[5] | 35.0% |

[1]by weight of starting alcohol
[2]by weight of C12 alcohol
[3]by weight of 2-alkyl branched C12 alcohol
[4]by weight of C13 alcohol
[5]by weight of 2-alkyl branched C13 alcohol
[6] such as alcohol isomers with alkyl chain-lengths other than 12 or 13 carbons.

The starting Alcohol Example 1 of Table 1 was individually sulfated in the pilot plant according to the process as set out above to provide the First Surfactant Example 1. The resulting alkyl sulfate distribution (Table 2) is retained and corresponds to the distribution of the alkyl chains as set out for the Alcohol Example 1 in Table 1. The data as shown in Table 2 are only indicative as measured by a not yet standardized UHPLC-CAD method.

TABLE 2

Indicative alkyl chain distribution of the first surfactant including a mixture of C12 and C13 alkyl sulfate anionic surfactants obtained from LIAL ®123A alcohol supplied by SASOL

| | First Surfactant Example 1 |
|---|---|
| Alkyl chain length | C12 |
| Total C12 Alkyl sulfate[1] | 45.2% |

TABLE 2-continued

Indicative alkyl chain distribution of the first surfactant including a mixture of C12 and C13 alkyl sulfate anionic surfactants obtained from LIAL ®123A alcohol supplied by SASOL

| | First Surfactant Example 1 |
|---|---|
| Linear content C12 Alkyl sulfate[1] | 21.6% |
| 2-Alkyl Branched C12 Alkyl sulfate[1] | 23.6% |
| 2-Alkyl Branch C12 distribution: | |
| 2-methyl-1-undecyl sulfate[1] | 7.7% |
| 2-ethyl-1-decyl sulfate[1] | 4.1% |
| 2-propyl-1-nonyl sulfate[1] | 4.3% |
| 2-butyl-1-octyl sulfate, 2-pentyl-1-heptyl sulfate, other 2-Alkyl Branched C12 Alkyl sulfate[1] | 7.5% |
| Alkyl chain length | C13 |
| Total C13 Alkyl sulfate[1] | 51.9% |
| Linear content C13 Alkyl sulfate[1] | 26.2% |
| 2-Alkyl Branched C13 Alkyl sulfate[1] | 25.7% |
| 2-Alkyl Branch C13 distribution: | |
| 2-methyl-1-dodecyl sulfate[1] | 9.1 |
| 2-ethyl-1-undecyl sulfate[1] | 3.9 |
| 2-propyl-1-decyl sulfate[1] | 3.9 |
| 2-butyl-1-nonyl sulfate, 2-pentyl-1-octyl sulfate, other 2-Alkyl Branched C13 Alkyl sulfate[1] | 8.8 |
| Other[1, 6] | 2.9% |
| TOTAL[1] | 100% |
| Degree of branching | 49.3% |
| Alkyl chain length | C12 |
| Linear content C12 Alkyl sulfate[2] | 47.8% |
| 2-Alkyl Branched C12 Alkyl sulfate[2] | 52.2% |
| Total C12 Alkyl sulfate[2] | 100% |
| 2-Alkyl Branched C12 distribution: | |
| 2-methyl-1-undecyl sulfate[3] | 32.6% |
| 2-ethyl-1-decyl sulfate[3] | 17.4% |
| 2-propyl-1-nonyl sulfate[3] | 18.2% |
| 2-butyl-1-octyl sulfate, 2-pentyl-1-heptyl sulfate, other 2-Alkyl Branched C12 Alkyl sulfate[3] | 31.8% |
| Alkyl chain length | C13 |
| Linear content C13 Alkyl sulfate[4] | 50.5% |
| 2-Alkyl Branched C13 Alkyl sulfate[4] | 49.5% |
| Total C13 Alkyl sulfate[4] | 100% |
| 2-Alkyl Branched C13 distribution: | |
| 2-methyl-1-dodecyl sulfate[5] | 35.4% |
| 2-ethyl-1-undecyl sulfate[5] | 15.2% |
| 2-propyl-1-decyl sulfate[5] | 15.2% |
| 2-butyl-1-nonyl sulfate, 2-pentyl-1-octyl sulfate, other 2-Alkyl Branched C13 Alkyl sulfate[5] | 34.2% |

[1]by weight of the first surfactant
[2]by weight of C12 alkyl sulfate
[3]by weight of 2-alkyl branched C12 alkyl sulfate
[4]by weight of C13 alkyl sulfate
[5]by weight of 2-alkyl branched C13 alkyl sulfate
[6] such as isomers with alkyl chain-lengths other than 12 or 13 carbons.

The Alcohol Example 2 was commercially available as tradename ISACHELM®123A alcohol supplied from SASOL and was analyzed by gas chromatography with flame ionization detection (GC/FID) as set out above. The alkyl chain distribution is provided in Table 3.

The starting Alcohol Example 2 of Table 3 was also individually sulfated in the pilot plant according to the process as set out above to provide the First Surfactant Example 2. The resulting alkyl sulfate distribution is retained and corresponds to the distribution of the alkyl chains as set out for the Alcohol Example 2.

TABLE 3

Alkyl chain distribution of starting Alcohol Example 2. ISALCHEM ®123A alcohol commercially available from SASOL

| | Alcohol Example 2 |
|---|---|
| Alkyl chain length | C12 |
| Total C12 Alcohol[1] | 42.8% |
| Alkyl chain length | C13 |
| Total C13 Alcohol[1] | 55.1% |
| Other[1, 6] | 2.1% |
| TOTAL[1] | 100% |
| Degree of branching | 92.6% |

Comparative First Surfactant

A comparative branched alkyl C13 alkyl sulfate as a comparative first surfactant has been prepared from tridecyl alcohol. Tridecyl alcohol was commercially available as Exxal®13 from Exxon Mobil.

The comparative branched alkyl C13 alkyl sulfate was made according the following process: Tridecyl alcohol commercially available as Tradename Exxal®13 from Exxon Mobil was sulfated in a falling film using a Chemithon single 15 mm×2 m tube reactor using $SO_3$ generated from a sulfur burning gas plant operating at 2.4 kg/h (5.3 lb/hr) sulfur to produce 3.56% $SO_3$ on a volume basis. Alcohol feed rate was 14.2 kg/hour (31.33 lb/hr) and feed temperature was 37.8° C. (100° F.). Conversion of the alcohol to alcohol sulfate acid mix was achieved with 97.75% completeness. Neutralization with 50% sodium hydroxide was completed at ambient process temperature to 0.55% excess sodium hydroxide. 124.9 L (33 gallons) of the sodium neutralized first surfactant sulfate paste. Analyses by standard Cationic $SO_3$ titration method determined final average product activity to be about 29%.

The resulting comparative branched alkyl C13 alkyl sulfate was further concentrated to 69%-71% activity for trying to make a concentrated personal cleansing composition.

The resulting comparative branched alkyl C13 alkyl sulfate had two phases as evidenced by microscopy: A smeared birefringent texture had been observed with a relatively high level of a dispersed crystalline phase (spherical with birefringent cross pattern). It is not uncommon for a material to have a crystalline phase at ambient temperature. This requires heated transportation and storage. However, even at 65° C. the comparative branched alkyl C13 alkyl sulfate still remains in two phases.

The rheology of the comparative branched alkyl C13 alkyl sulfate appears to make it unsuitable for manufacture and commercial use. It is a gel with a somewhat hard texture at all temperatures evaluated, which means it would be difficult to manufacture into a personal cleansing composition as claimed.

Also, notably, at a large scale, since the comparative branched alkyl C13 alkyl sulfate does not have a fluid rheology, it would be nearly impossible to manufacture the comparative branched alkyl C13 alkyl sulfate because of phase separation at the end of the sulfation process. Hence, there is a need to select a better first surfactant than can lead to a personal cleansing composition being a stable and rigid gel.

The following compositions were prepared and assessed. First, personal cleansing compositions were prepared using the First Surfactant Example 1. The First Surfactant Example 1 is the sulfated product prepared from the Alcohol Example 1 that was commercially available as tradename LIAL®123A alcohol supplied from SASOL.

Compositions (% wt.)

| | EXAMPLE | | | | | |
|---|---|---|---|---|---|---|
| | CEx 1 | CEx 2 | CEx 3 | Ex. 1 | Ex. 2 | Ex. 3 |
| First surfactant Example 1 | 16.99 | 22.69 | 28.23 | 31.08 | 33.95 | 30.97 |
| cocamidopropyl betaine | 2.52 | 3.38 | 4.22 | 4.70 | 5.09 | 4.65 |
| Dipropylene glycol | 12.94 | 12.94 | 12.95 | 13.00 | 12.96 | 9.84 |
| perfume | 32.48 | 26.01 | 19.73 | 16.33 | 13.02 | 19.42 |
| citric acid | 0.23 | 0.23 | 0.33 | 0.30 | 0.36 | 0.36 |
| water | | | q.s. | | | |
| Weight ratio total surfactant/ dipropylene glycol | 1.50 | 2.00 | 2.50 | 2.75 | 3.01 | 3.62 |
| Weight ratio perfume/total surfactant | 1.66 | 0.99 | 0.60 | 0.46 | 0.33 | 0.54 |
| total surfactant | 19.51 | 26.07 | 32.45 | 35.78 | 39.04 | 35.62 |
| observations | Transparent fluid | Transparent fluid | 2 phases | Weak gel holds air bubbles | Weak gel holds air bubbles | Lamellar gel |
| G' at 1 Hz (Pa) | Too low viscosity | Too low viscosity | — | — | — | 448 |
| G' at 1 Hz (Pa) | — | — | — | — | — | 67.7 |
| Tan delta | — | — | — | — | — | 0.15 |

| | EXAMPLE | | | | |
|---|---|---|---|---|---|
| | CEx 4 | CEx 5 | CEx 6 | CEx. 7 | CEx. 8 |
| First surfactant Example 1 | 31.06 | 16.80 | 16.89 | 33.81 | 22.53 |
| cocamidopropyl betaine | 4.67 | 2.50 | 2.50 | 5.10 | 3.38 |
| Dipropylene glycol | 19.45 | 19.34 | 32.49 | 19.47 | 19.44 |
| perfume | 9.72 | 25.85 | 13.06 | 6.64 | 19.44 |
| citric acid | 0.33 | 0.16 | 0.33 | 0.39 | 0.36 |
| water | | | q.s. | | |
| Weight ratio total surfactant/dipropylene glycol | 1.84 | 0.99 | 0.59 | 1.99 | 1.33 |
| Weight ratio perfume/total surfactant | 0.27 | 1.33 | 0.67 | 0.17 | 0.75 |
| total surfactant | 35.73 | 19.30 | 19.39 | 38.91 | 25.91 |
| observations | Transparent fluid | Transparent fluid | Transparent fluid | Transparent fluid | Transparent fluid |
| G' at 1 Hz (Pa) | Too low viscosity | Too low viscosity | Too low viscosity | Too low viscosity | Too low viscosity |

| | EXAMPLE | | | | |
|---|---|---|---|---|---|
| | Ex. 4 | Ex. 5 | Ex. 6 | CEx. 9 | CEx. 10 |
| First surfactant Example 1 | 36.68 | 39.46 | 36.72 | 33.94 | 33.81 |
| cocamidopropyl betaine | 5.54 | 5.91 | 5.48 | 5.08 | 5.05 |
| Dipropylene glycol | 13.00 | 11.68 | 14.68 | 16.27 | 14.90 |
| perfume | 9.80 | 7.83 | 8.07 | 9.67 | 11.11 |
| citric acid | 0.40 | 0.56 | 0.43 | 0.40 | 0.43 |
| water | | | q.s. | | |
| total surfactant | 42.22 | 45.37 | 42.20 | 39.02 | 38.85 |
| Weight ratio total surfactant/dipropylene glycol | 3.24 | 3.88 | 2.87 | 2.39 | 2.60 |
| Weight ratio perfume/total surfactant | 0.23 | 0.17 | 0.19 | 0.24 | 0.28 |

-continued

| Compositions (% wt.) | | | | | |
|---|---|---|---|---|---|
| observations | Lamellar gel | Lamellar gel | Weak gel holds air bubbles | 2 phases | 2 phases |
| G' at 1 Hz (Pa) | 257 | 598 | 30 | — | — |
| G' at 1 Hz (Pa) | 59.5 | 81.4 | 12.1 | — | — |
| Tan delta | 0.23 | 0.14 | 0.40 | — | — |

| | EXAMPLE | | | |
|---|---|---|---|---|
| | CEx. 11 | CEx. 12 | CEx. 13 | CEx. 14 |
| First surfactant Example 1 | 22.58 | 19.78 | 19.76 | 31.04 |
| cocamidopropyl betaine | 3.38 | 2.96 | 2.93 | 4.65 |
| Dipropylene glycol | 6.67 | 6.53 | 9.72 | 16.28 |
| perfume | 32.46 | 35.66 | 32.49 | 13.03 |
| citric acid | 0.23 | 0.23 | 0.30 | 0.33 |
| water | q.s. | | | |
| Weight ratio total surfactant/dipropylene glycol | 3.89 | 3.48 | 2.33 | 2.19 |
| Weight ratio perfume/total surfactant | 1.25 | 1.56 | 1.43 | 0.36 |
| total surfactant | 25.96 | 22.74 | 22.69 | 35.69 |
| observations | Weak gel holds air bubbles | Transparent fluid | Transparent fluid | 2 phases |
| G' at 1 Hz (Pa) | — | Too low viscosity | Too low viscosity | — |

It has been found that the compositions having an elastic modulus G' from about 100 Pa at 1 Hz do comprise significant lamellar phase and did not phase separate. For instance, Example 3 provided a stable gel having a stable lamellar phase as Example 3 did not phase separate, and had an elastic modulus G' of 448 Pa. The same observations could be found with Examples 4 and 5.

In some cases, the compositions may have an elastic modulus G' less than about 100 Pa such as Ex. 6 and still provide an acceptable lamellar phase. Ex. 6 appears to be a shelf stable gel when the elastic modulus G' is from about 25 Pa to less than 90 at 1 Hz.

It has been evidenced as shown in FIG. 1 that the personal cleansing composition as defined herein comprising the surfactant that comprises a first surfactant and a cosurfactant, needs to include:

from about 30% to about 55%, preferably from about 32% to about 52%, more preferably from about 35.5% to about 50% of a surfactant by weight of the composition;

from about 4.5% to about 25%, preferably from about 7% to about 22%, more preferably from about 7.5% to about 19.5% of a perfume by weight of the composition;

from about 6% to about 18.5%, preferably from about 6.5% to about 17%, more preferably from about 7% to about 15% of a hydric solvent by weight of the composition; and water.

Also, the weight ratio of the surfactant to the hydric solvent needs to be greater than or equal to 2.7, preferably greater than or equal to 3.1, more preferably greater than or equal to 3.8, even more preferably from 3.8 to 5.0.

Then, the personal cleansing composition is structured. At least a portion of the composition may be in a lamellar phase. The personal cleansing composition is therefore a stable and rigid gel and relatively concentrated.

Such stable and rigid gel can have a lamellar structure. The resulting personal cleansing composition has a relatively high content of perfume and specific levels of hydric solvent. The claimed personal cleansing composition can then deliver relatively high perfume levels to skin.

In other words, the personal cleansing composition is structured. The composition may have a lamellar composition comprising a relatively high content of perfume that can be delivered onto skin during cleansing due to combinations of the surfactant and hydric solvent as recited herein above.

The lamellar phase may be proximal to a microemulsion and/or the personal cleansing composition may have a microemulsion phase in equilibrium with a lamellar phase.

Thus, the personal cleansing compositions may not have to necessarily be in a single microemulsion phase. The personal cleansing compositions may comprise two phases with one phase being a microemulsion and another one being a lamellar phase.

It follows that the personal cleansing composition itself does not necessarily need to be or dilute to a microemulsion, but part of the personal cleansing composition may be a microemulsion.

When diluted during consumer use, the personal cleansing composition diluted to a microemulsion that delivers relatively high perfume levels onto skin.

As another example, the following compositions were prepared and assessed. Personal cleansing compositions were prepared using the First Surfactant Example 2. The First Surfactant Example 2 is the sulfated product prepared from the Alcohol Example 2 that was commercially available as tradename ISALCHEM®123A alcohol supplied from SASOL.

| Compositions (% wt.) | | | | |
|---|---|---|---|---|
| | EXAMPLE | | | |
| | CEx. 20 | CEx. 21 | CEx. 22 | CEx. 23 |
| First surfactant Example 2 | 16.96 | 16.96 | 16.96 | 22.61 |
| cocamidopropyl betaine | 2.54 | 2.54 | 2.54 | 3.39 |
| Dipropylene glycol | 13.00 | 19.50 | 32.50 | 13.00 |
| perfume | 32.50 | 26.00 | 13.00 | 26.00 |
| citric acid | 0.47 | 0.47 | 0.47 | 0.47 |
| water | q.s. | | | |
| Weight ratio total surfactant/dipropylene glycol | 1.50 | 1.00 | 0.60 | 2.00 |
| Weight ratio perfume/total surfactant | 1.67 | 1.33 | 0.67 | 1.00 |
| total surfactant | 19.50 | 19.50 | 19.50 | 26.00 |
| observations | Transparent fluid | Transparent fluid | Transparent fluid | Transparent fluid |
| G' at 1 Hz (Pa) | Too low viscosity | Too low viscosity | Too low viscosity | Too low viscosity |

| | EXAMPLE | | |
|---|---|---|---|
| | CEx. 24 | CEx. 25 | CEx. 26 |
| First surfactant Example 2 | 22.61 | 28.26 | 33.92 |
| cocamidopropyl betaine | 3.39 | 4.24 | 5.08 |
| Dipropylene glycol | 6.50 | 13.00 | 15.60 |
| perfume | 32.50 | 19.50 | 10.40 |
| citric acid | 0.47 | 0.47 | 0.47 |
| water | | q.s. | |
| Weight ratio total surfactant/dipropylene glycol | 4.00 | 2.50 | 2.50 |
| Weight ratio perfume/total surfactant | 1.25 | 0.60 | 0.26 |
| total surfactant | 26.00 | 32.50 | 39.00 |
| observations | Turbid fluid 2 phases | 2 phases | 2 phases |
| G' at 1 Hz (Pa) | — | — | — |

| | EXAMPLE | | | |
|---|---|---|---|---|
| | Ex. 20 | Ex. 21 | Ex. 22 | Ex. 23 |
| First surfactant Example 2 | 31.09 | 33.92 | 36.74 | 39.57 |
| cocamidopropyl betaine | 4.66 | 5.08 | 5.51 | 5.93 |
| Dipropylene glycol | 9.75 | 13.00 | 13.00 | 11.05 |
| perfume | 19.50 | 13.00 | 9.75 | 8.45 |
| citric acid | 0.47 | 0.47 | 0.47 | 0.47 |
| water | q.s. | | | |
| Weight ratio total surfactant/dipropylene glycol | 3.67 | 3.00 | 3.25 | 4.11 |
| Weight ratio perfume/total surfactant | 0.54 | 0.33 | 0.23 | 0.18 |
| total surfactant | 35.75 | 39.00 | 42.25 | 45.50 |
| observations | Lamellar gel | Lamellar gel | Lamellar gel | Lamellar gel |
| G' at 1 Hz (Pa) | 665 | 417 | 586 | 1186 |
| G" at 1 Hz (Pa) | 49.6 | 42.1 | 49.6 | 84.6 |
| Tan delta | 0.07 | 0.10 | 0.08 | 0.07 |

The same findings have been obtained with the First Surfactant Example 2 as when using the First surfactant Example 1 (See also FIG. 2).

Lx. 20-23 have also a relatively low Tan delta showing that the personal cleansing compositions are even better structured than comparative compositions with higher tan delta.

Perfume Headspace Abundance During Dilution

Two personal cleansing compositions Ex. A and Ex. B were prepared with the first surfactant Example 1, in addition to a micelle control (including sodium lauryl sulfate).

Each composition was diluted in steps with deionized water at water:composition weight ratio of 1.5, 2.0, 2.5, 3.0, 3.5, 4.5 ratio. The compositions tested were the following:

| | EXAMPLE | | Micelle control body |
|---|---|---|---|
| | Ex. A | Ex. B | wash |
| Sodium laureth-1 sulfate (SLE1S) | — | — | 8.50 |
| First surfactant Example 1 | 20.82 | 18.37 | — |
| cocamidopropyl betaine | 2.97 | 2.62 | 1.50 |
| Sodium chloride | — | — | 2.00 |
| Dipropylene glycol | 6.65 | 7.70 | — |
| perfume | 4.55 | 6.30 | 1.00 |
| citric acid | q.s. pH 6 | | 0.25 |
| water | q.s. | | q.s. |
| Weight ratio total surfactant/dipropylene glycol | 3.57 | 2.72 | — |
| Weight ratio perfume/total surfactant | 0.19 | 0.30 | 0.10 |
| total surfactant | 23.80 | 21.00 | 10.0 |
| observations | Lamellar gel | Lamellar gel | — |

GC-MS headspace over compositions in the dilution steps was measured as an indication of fragrance delivery during consumer use using the Perfume Headspace Abundance During Dilution Method (PHADD) as described hereinabove.

Typically, micelle compositions like conventional body wash deliver little fragrance to the skin, and micelle compositions dilute to lower headspace GCMS concentrations. Conversely, microemulsions rearrange the location of the fragrance and surfactant so that headspace concentrations of many perfume raw material (PRM) increase. During dilution, significantly increased headspace concentrations relative to the neat undiluted composition suggest microemulsion behavior.

The term "Perfume Raw Materials" as used herein refer to perfume materials or fragrances. The perfume raw material is characterized by its boiling point (B.P.) and its octanol/water partitioning coefficient (P). An octanol/water partition coefficient of a PRM is the ratio between its equilibrium concentrations in octanol and in water. The partition coefficients of the PRM used in a composition may more conveniently be given in the form of its logarithm to the base 10, Log P. The term "C log P" as used herein refers to a calculated log P ("C log P?") value of a PRM. The C log P is determined by a model that computes the octanol-water partition coefficient (log P or log Kow) for general organic molecules based directly on molecular structure. Log P is a measure of the distribution of a solute between two immiscible liquid phases, octanol and water, and is generally used as a relative measure of the hydrophobicity of a solute. One way of computing Log P of a PRM is using the ACD/Labs Log P software module from Advanced Chemistry Development, Inc. Details of the calculation of log P can be found on the ACD/Labs website (https://www.acdlabs.com/products/percepta/predictors/logp/). Log P values of PRMs calculating using the ACD/Labs Log P software module. Alternatively, it will be appreciated that another suitable way of measuring Log P is using the "C log P" program from BioByte Corp (e.g., C log P Version 4.0 and Manual 1999). CLOG P USER GUIDE, Version 4.0. BioByte Corp (1999) (http://www.bio-byte.com/bb/prod/clogp40.html). A further suitable way of measuring Log P is using C LOG P program from Daylight Chemical Information Systems, Inc. of Alison Viejo, CA. The C LOG P Reference manual, Daylight Version 4.9, Release Date Feb. 1, 2008.

Results

Figure 3:
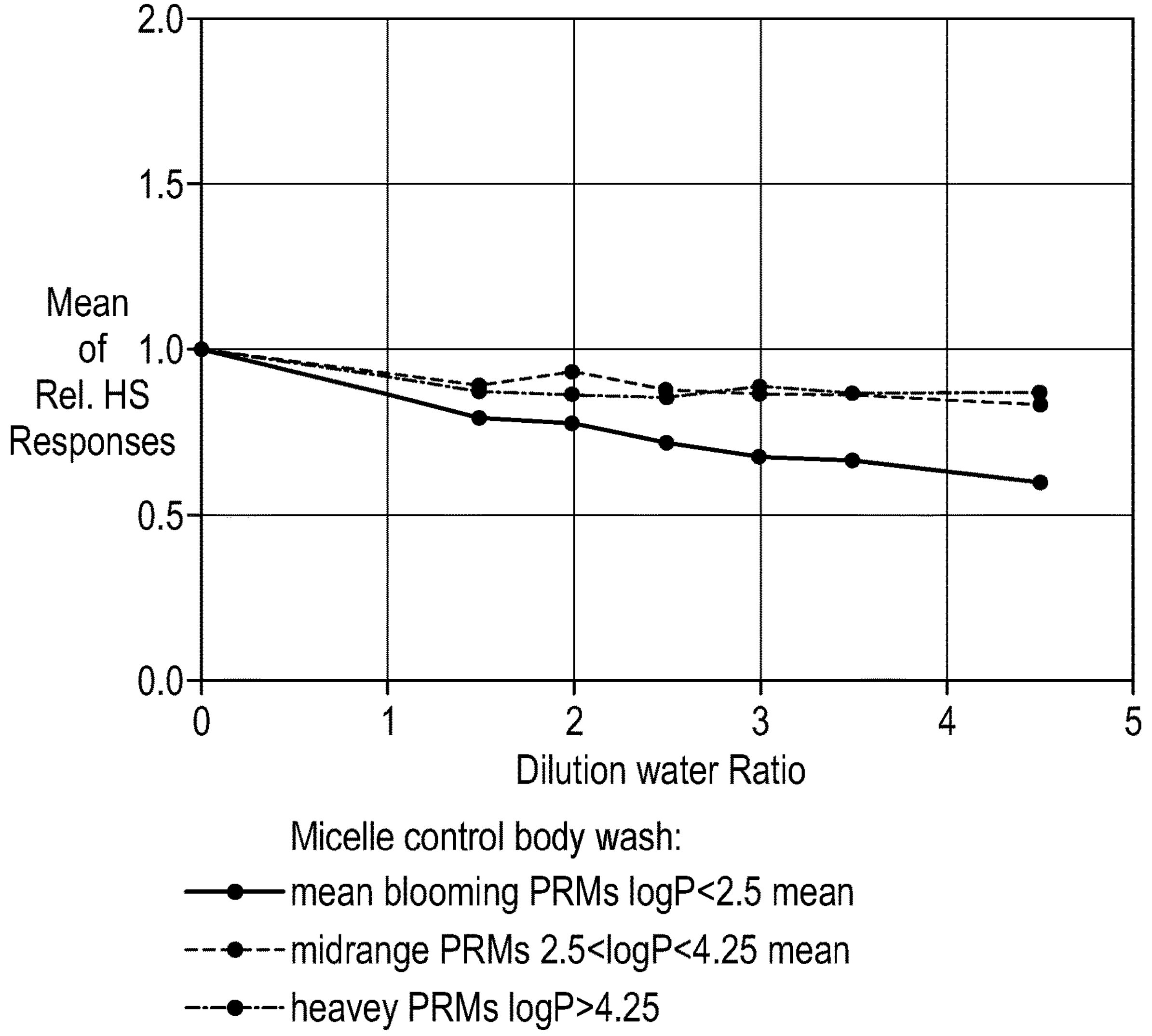
FIG. 3 provides means of relative headspace responses of a micelle control body wash upon dilution and in view of different PRMs log P ranges.
Figure 4:
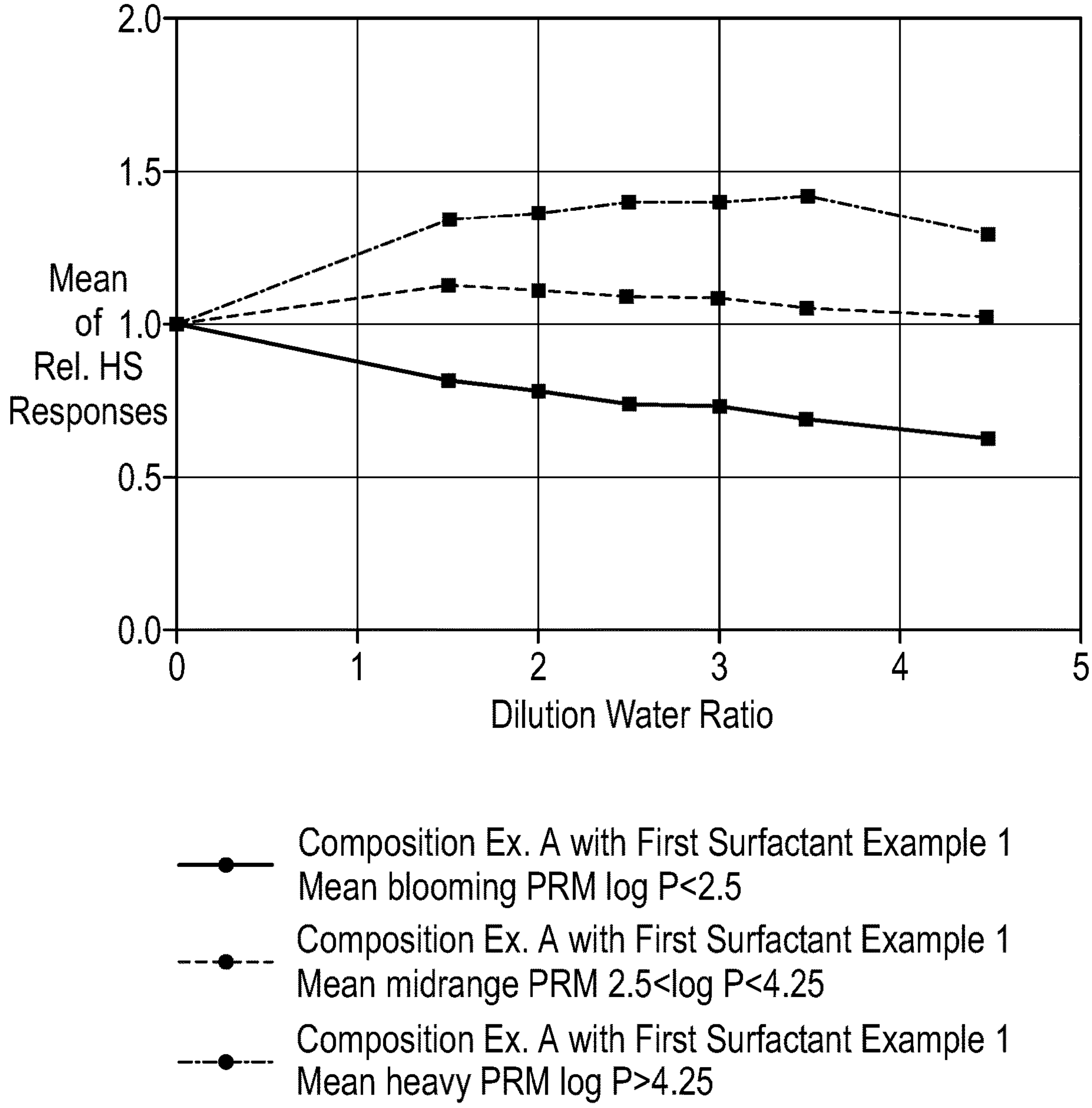
FIG. 4 provides means of relative headspace responses of a personal cleansing composition comprising a first surfactant upon dilution and in view of different PRMs log P ranges.

FIGS. 3 and 4 show the average headspace response of 70 fragrance molecules grouped into low, medium, high log P, which generally scales with 1/volatility. Results are normalized to the initial, undiluted composition. The micelle control body wash (FIG. 3) exhibits typical headspace behavior: dilution with water reduces concentration of perfume raw materials and less is evident in the headspace. The lowest log P PRM (which are most water soluble by definition) are reduced the most.

FIG. 4 shows for the microemulsion-tending compositions that Ex. A composition has elevated PRM concentration for the mid and high log P PRM, indicative of formation of a microemulsion. A similar result was obtained with composition Ex. B.

Dilution reduces the most water soluble PRM, but more hydrophobic PRM are elevated, indicating rearrangement of the solvent environment dissolving the perfume so that its concentration is higher—suggestive of microemulsion formation with these PRM migrating to form a microemulsion core.

Figure 5:
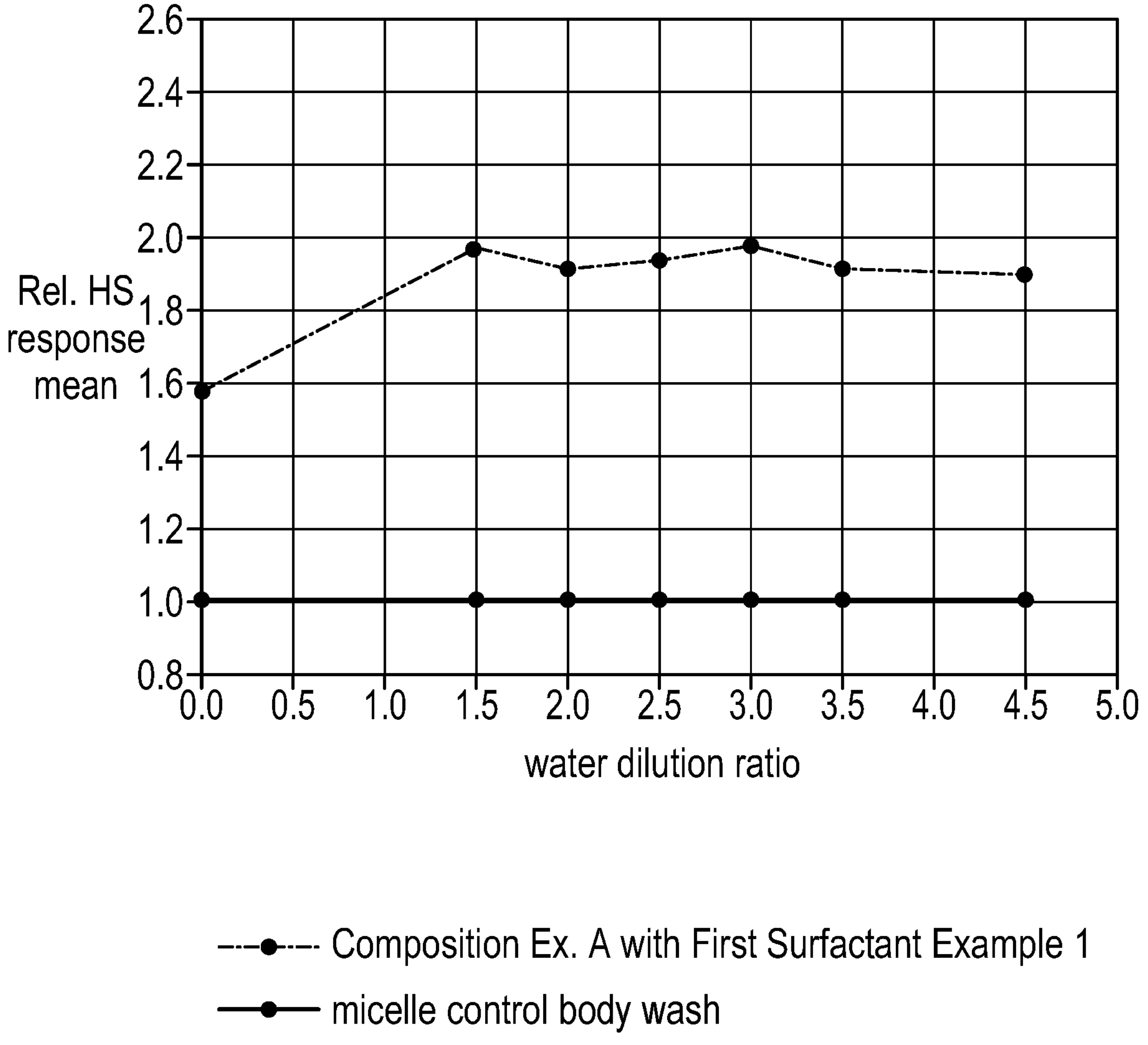
FIG. 5 provides an average headspace response of 70 PRM of a personal cleansing composition comprising a first surfactant compared to a control micelle composition at each dilution step tested.

FIG. 5 shows the personal cleansing composition comprising the first surfactant is normalized to the micelle formula instead of the neat undiluted, to show the difference these kinds of compositions demonstrate compared to a normal body wash.

The claimed personal cleansing compositions have two benefits: (1) the composition is structured such that there is a microemulsion behavior that increases the fragrance impact as it is diluted, and (2) there is also more fragrance in the composition compared to micelles. Both benefits combine to give the overall consumer benefit.

In FIG. 5, the PRM data are individually indexed to the micelle formula by dividing headspace concentrations, then averaged.

The claimed personal cleansing compositions are substantially greater than micelle body wash performance and give excellent in-use performance.

Figure 6:
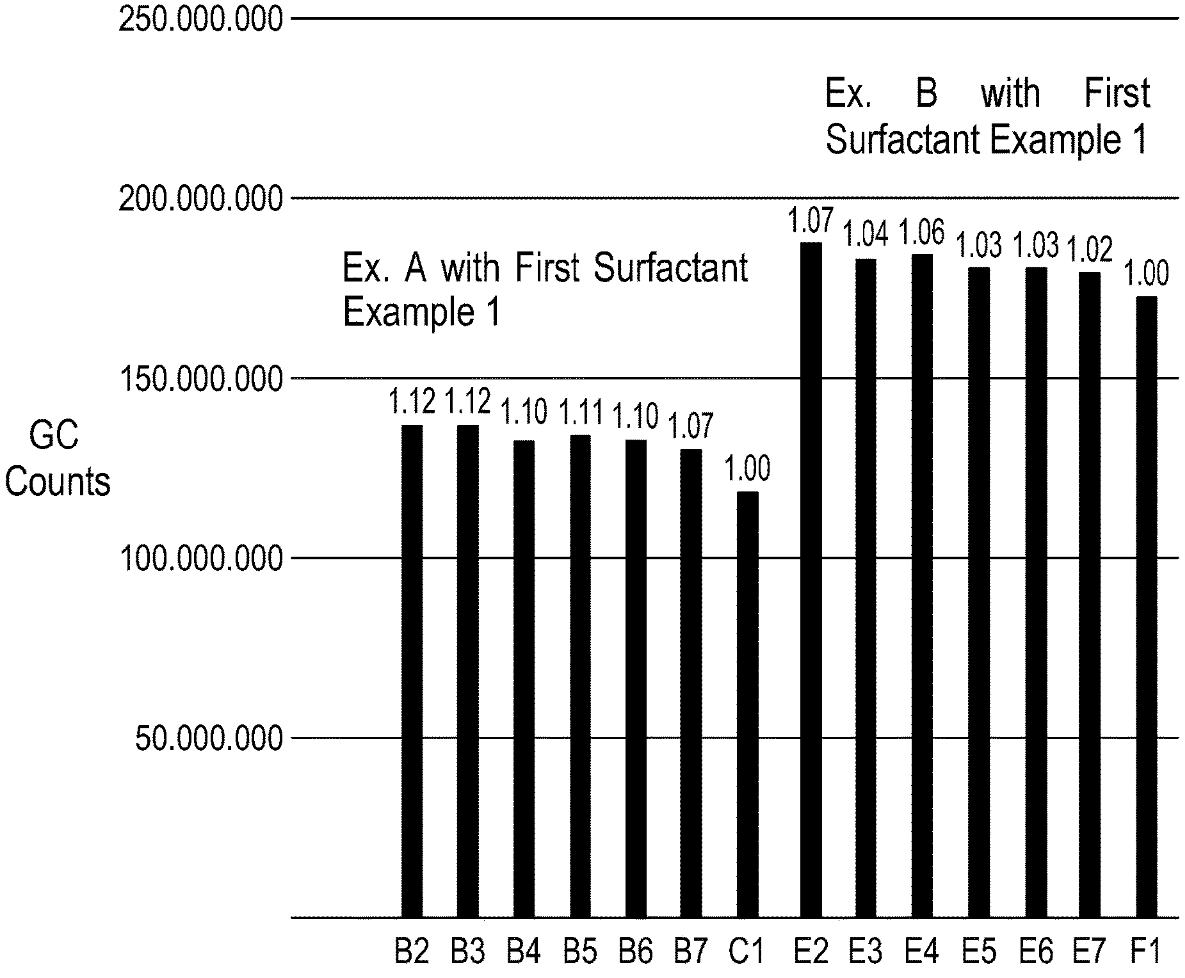
FIG. 6 shows a bar graph of the sum of all 70 PRM GC-MS headspace counts for a personal cleansing composition of the present invention.

FIG. 6 shows a bar graph of the sum of all 70 PRM GC-MS headspace counts. Each bar is also labelled with its relative response to its own undiluted control. More perfume in the personal cleansing compositions Ex. A and Ex. B also increased headspace PRM.

A characteristic of the personal cleansing composition diluted into a microemulsion is the partitioning behavior of different PRM into different locations in the microemulsion creates different PRM responses, according to where each PRM partitions. Microemulsions can be described by a pseudophase model, with three distinct compartments: a hydrophobic core, a surfactant film and an external aqueous compartment. PRM can partition into (i) the aqueous compartment on the outside, (ii) the palisade layer among the surfactant chains, or (iii) for the microemulsion only, in the central core region. In compartment (i) and (ii), PRM will be diluted by water and surfactant as 'solvents', reducing chemical potential and the perfume impact will be lower. While there are general trends, such as the core region being most hydrophobic and aqueous compartment most hydrophilic, prediction of the location of 70 unique PRM as a mixture in these compositions is not possible. The GC-MS headspace response gives us indirect insight into the solvent environment of the individual PRM.

Additional Examples/Combinations

A. A personal cleansing composition comprising: i) from 30% to 55%, preferably from 32% to 52%, more preferably from 35% to 50% of a surfactant by weight of the composition, wherein the surfactant comprises a first surfactant and a cosurfactant, wherein the first surfactant comprises a mixture of C12 and C13 alkyl sulfate anionic surfactants, optionally wherein the first surfactant consists essentially of a mixture of C12 and C13 alkyl sulfate anionic surfactants; wherein the mixture of the C12 and C13 alkyl sulfate anionic surfactants comprises a mixture of surfactant isomers of Formula I and surfactant isomers of Formula II:

$$CH_3-(CH_2)_p-CH_2-OSO_3^- X^+ \quad (I)$$

(II)

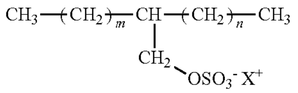

wherein 10≤p≤11; wherein 8≤m+n≤9 and 0≤m, n≤9; wherein X is a counter cation selected from the group consisting of lithium, sodium, potassium and ammonium, preferably sodium; wherein the first surfactant comprises: from 37% to 50%, preferably from 38% to 49%, more preferably from 40% to 49% of the C12 alkyl sulfate anionic surfactant by weight of the first surfactant, wherein the C12 alkyl sulfate anionic surfactant comprises a 2-alkyl branched C12 alkyl sulfate; from 50% to 63%, preferably from 51% to 62%, more preferably from 51% to 60% of the C13 alkyl sulfate anionic surfactant by weight of the first surfactant, wherein the C13 alkyl sulfate anionic surfactant comprises a 2-alkyl branched C13 alkyl sulfate; and less or equal than 5% of other alkyl sulfate anionic surfactants by weight of the first surfactant, preferably less or equal than 4% of other alkyl sulfate anionic surfactants by weight of the first surfactant, preferably wherein other alkyl sulfate anionic surfactants are not C12 or C13 alkyl sulfate anionic surfactant; ii) from 4.5% to 25%, preferably from 7% to 22%, more preferably from 7.5% to 19.5% of a perfume by weight of the composition; iii) from 6% to 18.5%, preferably from 6.5% to 17%, more preferably from 7% to 15% of a hydric solvent by weight of the composition; and iv) water; wherein the weight ratio of the surfactant to the hydric solvent is greater than or equal to 2.7, preferably greater than or equal to 3.1, more preferably greater than or equal to 3.8, even more preferably from 3.8 to 5.0; wherein the composition is structured, preferably at least a portion of the composition is in a lamellar phase.

B. The personal cleansing composition of Paragraph A, wherein the personal cleansing composition is a shelf-stable gel, preferably a stable gel; and has an elastic modulus G' at 1 Hz from about 30 Pa to about 2500 Pa, preferably from about 100 Pa to about 2000, more preferably from about 250 Pa to about 1500 Pa, even more preferably from about 250 Pa to about 1200 Pa, most preferably from 250 Pa to 775 Pa according to the G' and G" Test Method as disclosed herein.

C. The personal cleansing composition of any preceding paragraphs, wherein the first surfactant has an average degree of branching of greater than 90% or from 40% to 60% by weight, preferably from 45% to 55% by weight, more preferably from 46% to 54% by weight, most preferably from 48% to 54%.

D. The personal cleansing composition of any preceding paragraphs, wherein the C12 alkyl sulfate anionic surfactant of the first surfactant consists of: a) less than about 10%, preferably less than about 9%, more preferably from about 0% to about 8% of a linear C12 alkyl sulfate by weight of the C12 alkyl sulfate anionic surfactant; b) more than about 90%, preferably more than about 91%, more preferably from about 92% to about 100% of a 2-alkyl branched C12 alkyl sulfate by weight of the C12 alkyl sulfate anionic surfactant, wherein the 2-alkyl branched C12 alkyl sulfate comprises: more than about 25% of 2-methyl undecyl sulfate by weight the 2-alkyl branched C12 alkyl sulfate; and about 25% or less of 2-ethyl decyl sulfate by weight of the 2-alkyl-branched C12 alkyl sulfate; and c) from about 0% to about 5% of other branched C12 alkyl sulfates by weight of the C12 alkyl sulfate anionic surfactant wherein a), b) and c) add up to about 100% by weight of the C12 alkyl sulfate anionic surfactant.

E. The personal cleansing composition of any ones of paragraphs A-C, wherein the C12 alkyl sulfate anionic surfactant of the first surfactant consists of: a) less than 70% of a linear C12 alkyl sulfate by weight of the C12 alkyl sulfate anionic surfactant; b) more than 30% of a 2-alkyl branched C12 alkyl sulfate by weight of the C12 alkyl sulfate anionic surfactant, wherein the 2-alkyl branched C12 alkyl sulfate comprises: more than 25% of 2-methyl undecyl sulfate by weight the 2-alkyl branched C12 alkyl sulfate; and 25% or less of 2-ethyl decyl sulfate by weight of the 2-alkyl-branched C12 alkyl sulfate; and c) less than 10% of other branched C12 alkyl sulfates by weight of the C12 alkyl sulfate anionic surfactant; wherein a), b) and c) add up to 100% by weight of the C12 alkyl sulfate anionic surfactant.

F. The personal cleansing composition according to paragraph E, wherein the C12 alkyl sulfate anionic surfactant consists of: a) less than or equal to 60%, preferably from 45% to 55%, more preferably from 45% to 51% of the linear C12 alkyl sulfate by weight of the C12 alkyl sulfate anionic surfactant; b) more than or equal to 40%, preferably from 45% to 55%, more preferably from 49% to 55% of the 2-alkyl branched C12 alkyl sulfate by weight of the C12 alkyl sulfate anionic surfactant; and c) less than 10%, preferably from 0% to 5% of other branched C12 alkyl sulfates by weight of the C12 alkyl sulfate anionic surfactant; wherein a), b) and c) add up to 100% by weight of the C12 alkyl sulfate anionic surfactant.

G. The personal cleansing composition according to any ones of paragraphs E-F, wherein the 2-alkyl branched C12 alkyl sulfate comprises: more than 30%, preferably from 30.5% to 35% of 2-methyl undecyl sulfate by weight of the 2-alkyl branched C12 alkyl sulfate; less than 20%, preferably from 15% to 19.5% of 2-ethyl decyl sulfate by weight of the 2-alkyl branched C12 alkyl sulfate; less than 20%, preferably from 15% to 19.5% of 2-propyl nonyl sulfate by weight of the 2-alkyl branched C12 alkyl sulfate; and more than 25%, preferably from 26% to 35% of 2-butyl octyl sulfate and 2-pentyl heptyl sulfate and other 2-alkyl branched C12 alkyl sulfates by weight of the 2-alkyl branched C12 alkyl sulfate.

H. The personal cleansing composition of paragraph D, wherein the C13 alkyl sulfate anionic surfactant of the first surfactant consists of: d) less than about 10%, preferably less than about 9%, more preferably from about 0% to about 8% of a linear C13 alkyl sulfate by weight of the C13 alkyl sulfate anionic surfactant, and e) more than about 90%, preferably more than about 91%, more preferably from about 92% to about 100% of a 2-alkyl branched C13 alkyl sulfate by weight of the C13 alkyl sulfate anionic surfactant, wherein the 2-alkyl branched C13 alkyl sulfate comprises: more than about 30% of 2-methyl dodecyl sulfate by weight the 2-alkyl branched C13 alkyl sulfate, and about 25% or less of 2-ethyl undecyl sulfate by weight of the 2-alkyl branched C13 alkyl sulfate; and f) from about 0% to about 5% of other branched C13 alkyl sulfates by weight of the C13 alkyl sulfate anionic surfactant; wherein d), e) and f) add up to about 100% by weight of the C13 alkyl sulfate anionic surfactant.

I. The personal cleansing composition of any ones of paragraphs E-G, wherein the C13 alkyl sulfate anionic surfactant of the first surfactant consists of: d) less than 60% of a linear C13 alkyl sulfate by weight of the C13 alkyl sulfate anionic surfactant, and e) more than 40% of a 2-alkyl branched C13 alkyl sulfate by weight of the C13 alkyl sulfate anionic surfactant, wherein the 2-alkyl branched C13 alkyl sulfate comprises: more than 30% of 2-methyl dodecyl sulfate by weight the 2-alkyl branched C13 alkyl sulfate, and 25% or less of 2-ethyl undecyl sulfate by weight of the 2-alkyl branched C13 alkyl sulfate; and f) less than 10% of other branched C13 alkyl sulfates by weight of the C13 alkyl sulfate anionic surfactant; wherein d), e) and f) add up to 100% by weight of the C13 alkyl sulfate anionic surfactant.

J. The personal cleansing composition according to paragraph I, wherein the C13 alkyl sulfate anionic surfactant consists of: d) less than 55%, preferably from 45% to 54%, more preferably from 48% to 53% of the linear C13 alkyl sulfate by weight of the C13 alkyl sulfate anionic surfactant; e) more than 45%, preferably from 46% to 55%, more preferably from 47% to 52% of the 2-alkyl branched C13 alkyl sulfate by weight of the C13 alkyl sulfate anionic surfactant; and f) less than 10%, preferably from 0% to 5% of other branched C13 alkyl sulfates by weight of the C13 alkyl sulfate anionic surfactant; wherein d), e) and f) add up to 100% by weight of the C13 alkyl sulfate anionic surfactant.

K. The personal cleansing composition according to any ones of paragraphs I-J, wherein the 2-alkyl branched C13 alkyl sulfate comprises: more than 30.5%, preferably from 31% to 40% of 2-methyl dodecyl sulfate by weight of the 2-alkyl branched C13 alkyl sulfate; less than 20%, preferably from 10% to 18% of 2-ethyl undecyl sulfate by weight of the 2-alkyl branched C13 alkyl sulfate; less than 20%, preferably from 10% to 18% of 2-propyl decyl sulfate by weight of the 2-alkyl branched C13 alkyl sulfate; and more than 25%, preferably from 26% to 40% of 2-butyl nonyl sulfate and 2-pentyl octyl sulfate and other 2-alkyl branched C13 alkyl sulfates by weight of the 2-alkyl branched C13 alkyl sulfate.

L. The personal cleansing composition of any preceding paragraphs, wherein the personal cleansing composition is substantially free or free of alkoxylated anionic sulfate surfactant; preferably wherein the personal cleansing composition is substantially free or free of ethoxylated anionic sulfate surfactant.

M. The personal cleansing composition of any preceding paragraphs, wherein the surfactant further comprises from 2.5% to 10%, preferably from 3% to 7.75%, more preferably from 4.5% to 6.75% of a cosurfactant by weight of the composition, wherein the cosurfactant is selected from the group consisting of a zwitterionic surfactant, an amphoteric surfactant, a nonionic surfactant, and a combination thereof, preferably wherein the cosurfactant comprises a betaine, an alkyl amidopropyl betaine, cocoamidopropyl betaine, or a combination thereof.

N. The personal cleansing composition of any preceding paragraphs, wherein the weight ratio of the first surfactant to the cosurfactant is from 4:1 to 20:1, preferably from 5:1 to 9:1, more preferably from 6:1 to 8:1.

O. The personal cleansing composition of any preceding paragraphs, wherein the composition comprises from 6.5% to 59%, preferably from 16% to 54.5%, more preferably from 25% to 45% of water by weight of the composition.

P. The personal cleansing comprising of any preceding paragraphs, wherein the hydric solvent is selected from the group consisting of dipropylene glycol, diethylene glycol, dibutylene glycol, hexylene glycol, butylene glycol, pentylene glycol, heptylene glycol, propylene glycol, a polyethylene glycol having a weight average molecular weight below 500, and a combination thereof, preferably dipropylene glycol.

Q. The personal cleansing comprising of any preceding paragraphs, wherein at least a portion of the composition becomes a microemulsion upon dilution with water of 3:1 by weight (water:composition) to 10:1 by weight (water:composition).

R. A method of providing similar or enhanced in-vitro bloom or fragrance skin deposition of a rinse-off microemulsion cleansing composition, comprising, a synergistic combination of a first surfactant and a hydric solvent, including: i) from 30% to 55%, preferably from 32% to 52%, more preferably from 35% to 50% of a surfactant by weight of the composition, wherein the surfactant comprises a first surfactant and a cosurfactant, wherein the first surfactant comprises a mixture of C12 and C13 alkyl sulfate anionic surfactants, optionally wherein the first surfactant consists essentially of a mixture of C12 and C13 alkyl sulfate anionic surfactants; wherein the mixture of the C12 and C13 alkyl sulfate anionic surfactants comprises a mixture of surfactant isomers of Formula I and surfactant isomers of Formula II:

$$CH_3-(CH_2)_p-CH_2-OSO_3^- X^+ \quad (I)$$

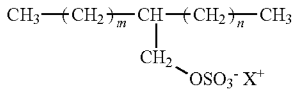

(II)

wherein 10≤p≤11; wherein 8≤m+n≤9 and 0≤m, n≤9; wherein X is a counter cation selected from the group consisting of lithium, sodium, potassium and ammonium, preferably sodium; wherein the first surfactant comprises: from 37% to 50%, preferably from 38% to 49%, more preferably from 40% to 49% of the C12 alkyl sulfate anionic surfactant by weight of the first surfactant, wherein the C12 alkyl sulfate anionic surfactant comprises a 2-alkyl branched C12 alkyl sulfate; from 50% to 63%, preferably from 51% to 62%, more preferably from 51% to 60% of the C13 alkyl sulfate anionic surfactant by weight of the first surfactant, wherein the C13 alkyl sulfate anionic surfactant comprises a 2-alkyl branched C13 alkyl sulfate; and less or equal than 5% of other alkyl sulfate anionic surfactants by weight of the first surfactant, preferably less or equal than 4% of other alkyl sulfate anionic surfactants by weight of the first surfactant, preferably wherein other alkyl sulfate anionic surfactants are not C12 or C13 alkyl sulfate anionic surfactant; ii) from 4.5% to 25%, preferably from 7% to 22%, more preferably from 7.5% to 19.5% of a perfume by weight of the composition; iii) from 6% to 18.5%, preferably from 6.5% to 17%, more preferably from 7% to 15% of a hydric solvent by weight of the composition; wherein the weight ratio of the surfactant to the hydric solvent is greater than or equal to 2.7, preferably greater than or equal to 3.0, more preferably greater than or equal to 3.8, even more preferably from 3.8 to 5.0; and water to obtain a personal cleansing composition containing a microemulsion phase; then diluting the personal cleansing composition with water at a weight ratio water:composition from 2:1 to 10:1, preferably from 3:1 to 10:1, more preferably from 5:1 to 8:1 to form a rinse-off microemulsion cleansing composition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal cleansing composition comprising:

i) from about 30% to about 55% of a surfactant by weight of the composition, wherein the surfactant comprises a first surfactant and a cosurfactant, wherein the first surfactant comprises a mixture of C12 and C13 alkyl sulfate anionic surfactants, wherein the mixture of the C12 and C13 alkyl sulfate anionic surfactants comprises a mixture of surfactant isomers of Formula I and surfactant isomers of Formula II:

$$CH_3-(CH_2)_p-CH_2-OSO_3^- X^+ \quad (I)$$

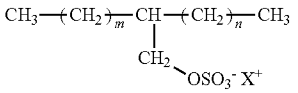

(II)

wherein 10≤p≤11;

wherein 8≤m+n≤9 and 0≤m, n≤9;

wherein X is a counter cation chosen from lithium, sodium, potassium, ammonium, or mixtures thereof;

wherein the first surfactant comprises:

from about 37% to about 50% of the C12 alkyl sulfate anionic surfactant by weight of the first surfactant, wherein the C12 alkyl sulfate anionic surfactant comprises a 2-alkyl branched C12 alkyl sulfate;

from about 50% to about 63% of the C13 alkyl sulfate anionic surfactant by weight of the first surfactant, wherein the C13 alkyl sulfate anionic surfactant comprises a 2-alkyl branched C13 alkyl sulfate;

and less or equal than about 5% of other alkyl sulfate anionic surfactants by weight of the first surfactant;

ii) from about 4.5% to about 25% of a perfume by weight of the composition;

iii) from about 6% to about 18.5% of a hydric solvent by weight of the composition, wherein the hydric solvent is a neutral organic species that contains at least 2 hydroxyl groups; and iv) water;

wherein the weight ratio of the surfactant to the hydric solvent is greater than or equal to 2.7;

wherein the composition is structured; and wherein the personal cleansing composition is substantially free of or free of ethoxylated anionic sulfate surfactant.

2. The personal cleansing composition of claim 1, wherein the personal cleansing composition is a stable gel and has an elastic modulus G' at 1 Hz from about 30 Pa to about 2500 Pa according to the G' and G" Test Method.

3. The personal cleansing composition of claim 1, wherein the first surfactant has an average degree of branching of greater than 90% by weight.

4. The personal cleansing composition of claim 1, wherein the C12 alkyl sulfate anionic surfactant of the first surfactant consists of:

a) less than about 10% of a linear C12 alkyl sulfate by weight of the C12 alkyl sulfate anionic surfactant;

b) more than about 90% of a 2-alkyl branched C12 alkyl sulfate by weight of the C12 alkyl sulfate anionic surfactant, wherein the 2-alkyl branched C12 alkyl sulfate comprises:

more than about 25% of 2-methyl undecyl sulfate by weight the 2-alkyl branched C12 alkyl sulfate; and about 25% or less of 2-ethyl decyl sulfate by weight of the 2-alkyl-branched C12 alkyl sulfate; and c) from 0% to about 5% of other branched C12 alkyl sulfates by weight of the C12 alkyl sulfate anionic surfactant;

wherein a, b and c add up to 100% by weight of the C12 alkyl sulfate anionic surfactant.

5. The personal cleansing composition of claim 1, wherein the C12 alkyl sulfate anionic surfactant of the first surfactant consists of:

a) less than about 70% of a linear C12 alkyl sulfate by weight of the C12 alkyl sulfate anionic surfactant;

b) more than about 30% of a 2-alkyl branched C12 alkyl sulfate by weight of the C12 alkyl sulfate anionic surfactant, wherein the 2-alkyl branched C12 alkyl sulfate comprises:

more than about 25% of 2-methyl undecyl sulfate by weight the 2-alkyl branched C12 alkyl sulfate; and about 25% or less of 2-ethyl decyl sulfate by weight of the 2-alkyl-branched C12 alkyl sulfate; and c) less than about 10% of other branched C12 alkyl sulfates by weight of the C12 alkyl sulfate anionic surfactant;

wherein a, b and c add up to 100% by weight of the C12 alkyl sulfate anionic surfactant.

6. The personal cleansing composition according to claim 5, wherein the C12 alkyl sulfate anionic surfactant consists of:

a) less than or equal to about 60% of the linear C12 alkyl sulfate by weight of the C12 alkyl sulfate anionic surfactant;

b) more than or equal to about 40% of the 2-alkyl branched C12 alkyl sulfate by weight of the C12 alkyl sulfate anionic surfactant; and c) less than about 10% of other branched C12 alkyl sulfates by weight of the C12 alkyl sulfate anionic surfactant;

wherein a, b and c add up to 100% by weight of the C12 alkyl sulfate anionic surfactant.

7. The personal cleansing composition according to claim 6, wherein the 2-alkyl branched C12 alkyl sulfate comprises:

more than about 30% of 2-methyl undecyl sulfate by weight of the 2-alkyl branched C12 alkyl sulfate;

less than about 20% of 2-ethyl decyl sulfate by weight of the 2-alkyl branched C12 alkyl sulfate;

less than about 20% of 2-propyl nonyl sulfate by weight of the 2-alkyl branched C12 alkyl sulfate; and more than about 25% of 2-butyl octyl sulfate and 2-pentyl heptyl sulfate and other 2-alkyl branched C12 alkyl sulfates by weight of the 2-alkyl branched C12 alkyl sulfate.

8. The personal cleansing composition of claim 1, wherein the C13 alkyl sulfate anionic surfactant of the first surfactant consists of:

a) less than about 10% of a linear C13 alkyl sulfate by weight of the C13 alkyl sulfate anionic surfactant, and b) more than about 90% of a 2-alkyl branched C13 alkyl sulfate by weight of the C13 alkyl sulfate anionic surfactant, wherein the 2-alkyl branched C13 alkyl sulfate comprises:

more than about 30% of 2-methyl dodecyl sulfate by weight the 2-alkyl branched C13 alkyl sulfate, and about 25% or less of 2-ethyl undecyl sulfate by weight of the 2-alkyl branched C13 alkyl sulfate; and c) from 0% to about 5% of other branched C13 alkyl sulfates by weight of the C13 alkyl sulfate anionic surfactant;

wherein a, b, and c add up to 100% by weight of the C13 alkyl sulfate anionic surfactant.

9. The personal cleansing composition of claim 1, wherein the C13 alkyl sulfate anionic surfactant of the first surfactant consists of:

a) less than about 60% of a linear C13 alkyl sulfate by weight of the C13 alkyl sulfate anionic surfactant, and b) more than about 40% of a 2-alkyl branched C13 alkyl sulfate by weight of the C13 alkyl sulfate anionic surfactant, wherein the 2-alkyl branched C13 alkyl sulfate comprises:

more than about 30% of 2-methyl dodecyl sulfate by weight the 2-alkyl branched C13 alkyl sulfate, and about 25% or less of 2-ethyl undecyl sulfate by weight of the 2-alkyl branched C13 alkyl sulfate; and c) less than about 10% of other branched C13 alkyl sulfates by weight of the C13 alkyl sulfate anionic surfactant;

wherein a, b, and c add up to 100% by weight of the C13 alkyl sulfate anionic surfactant.

10. The personal cleansing composition according to claim 9, wherein the C13 alkyl sulfate anionic surfactant consists of:

a) less than about 55% of the linear C13 alkyl sulfate by weight of the C13 alkyl sulfate anionic surfactant;

b) more than about 45% of the 2-alkyl branched C13 alkyl sulfate by weight of the C13 alkyl sulfate anionic surfactant; and c) less than about 10% of other branched C13 alkyl sulfates by weight of the C13 alkyl sulfate anionic surfactant;

wherein a, b, and c add up to 100% by weight of the C13 alkyl sulfate anionic surfactant.

11. The personal cleansing composition according to claim 10, wherein the 2-alkyl branched C13 alkyl sulfate comprises:

more than about 30.5% of 2-methyl dodecyl sulfate by weight of the 2-alkyl branched C13 alkyl sulfate;

less than about 20% of 2-ethyl undecyl sulfate by weight of the 2-alkyl branched C13 alkyl sulfate;

less than about 20% of 2-propyl decyl sulfate by weight of the 2-alkyl branched C13 alkyl sulfate; and more than about 25% of 2-butyl nonyl sulfate and 2-pentyl octyl sulfate and other 2-alkyl branched C13 alkyl sulfates by weight of the 2-alkyl branched C13 alkyl sulfate.

12. The personal cleansing composition according to claim 1, wherein the surfactant further comprises from about 2.5% to about 10% of the cosurfactant by weight of the composition.

13. The personal cleansing composition according to claim 12, wherein the weight ratio of the first surfactant to the cosurfactant is from about 4:1 to about 20:1.

14. The personal cleansing composition according to claim 12, wherein the cosurfactant comprises a betaine, an alkyl amidopropyl betaine, cocoamidopropyl betaine, or a combination thereof.

15. The personal cleansing composition according to claim 1, wherein the composition contains a microemulsion phase, wherein the microemulsion phase is in equilibrium with a lamellar phase.

16. The personal cleansing comprising according to claim 1, wherein the hydric solvent is chosen from dipropylene glycol, diethylene glycol, dibutylene glycol, hexylene glycol, butylene glycol, pentylene glycol, heptylene glycol, propylene glycol, a polyethylene glycol having a weight average molecular weight below about 500, or mixtures thereof.

17. The personal cleansing comprising according to claim 1, wherein the composition is not a ringing gel.

18. The personal cleansing comprising according to claim 1, wherein at least a portion of the composition becomes a microemulsion upon dilution with a weight ratio of water to composition of about 3:1 to about 10:1.

19. A method of providing in-vitro bloom or fragrance skin deposition of a rinse-off microemulsion cleansing composition, comprising, a combination of a first surfactant and a hydric solvent, including:

from about 30% to about 55% of a surfactant by weight of the composition, wherein the surfactant comprises a first surfactant and a cosurfactant, wherein the first surfactant comprises a mixture of C12 and C13 alkyl sulfate anionic surfactants, wherein the mixture of the C12 and C13 alkyl sulfate anionic surfactants comprises a mixture of surfactant isomers of Formula I and surfactant isomers of Formula II:

$$CH_3-(CH_2)_p-CH_2-OSO_3^- X^+ \quad (I)$$

(II)

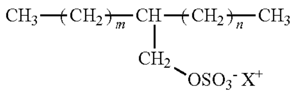

wherein 10≤p≤11;

wherein 8≤m+n≤9 and 0≤m, n≤9;

wherein X is a counter cation chosen from lithium, sodium, potassium, ammonium, or mixtures thereof;

wherein the first surfactant comprises:

from about 37% to about 50% of the C12 alkyl sulfate anionic surfactant by weight of the first surfactant, wherein the C12 alkyl sulfate anionic surfactant comprises a 2-alkyl branched C12 alkyl sulfate;

from about 50% to about 63% of the C13 alkyl sulfate anionic surfactant by weight of the first surfactant, wherein the C13 alkyl sulfate anionic surfactant comprises a 2-alkyl branched C13 alkyl sulfate;

and less or equal than about 5% of other alkyl sulfate anionic surfactants by weight of the first surfactant;

ii) from about 4.5% to about 25% of a perfume by weight of the composition;

iii) from about 6% to about 18.5% of a hydric solvent by weight of the composition;

wherein the weight ratio of the surfactant to the hydric solvent is greater than or equal to 2.7, wherein the hydric solvent is a neutral organic species that contains at least 2 hydroxyl groups and is not a hydrotrope; and water to obtain a personal cleansing composition containing a microemulsion phase, and wherein the personal cleansing composition is substantially free of or free of ethoxylated anionic sulfate surfactant;

then diluting the personal cleansing composition with water at a weight ratio water: composition from about 2:1 to about 10:1 to form a rinse-off microemulsion cleansing composition.

* * * * *